(12) United States Patent
Kane et al.

(10) Patent No.: US 10,952,621 B2
(45) Date of Patent: Mar. 23, 2021

(54) MULTIMODAL ANALYTE SENSOR OPTOELECTRONIC INTERFACE

(71) Applicant: Cardiac Pacemakers, Inc., St. Paul, MN (US)

(72) Inventors: Michael J. Kane, St. Paul, MN (US); Keith R. Maile, New Brighton, MN (US); Yingbo Li, Shanghai (CN); Jean M. Bobgan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 137 days.

(21) Appl. No.: 16/136,773

(22) Filed: Sep. 20, 2018

(65) Prior Publication Data

US 2019/0167112 A1  Jun. 6, 2019

(51) Int. Cl.
*A61B 5/00* (2006.01)
*G01N 21/63* (2006.01)
(Continued)

(52) U.S. Cl.
CPC .......... *A61B 5/0086* (2013.01); *A61B 5/1459* (2013.01); *A61B 5/14546* (2013.01);
(Continued)

(58) Field of Classification Search
CPC ............. A61B 5/1455; A61B 5/14532; A61B 5/1459; A61B 5/14545; A61B 5/1473; A61B 5/6846; A61B 5/686; A61B 5/6861
See application file for complete search history.

(56) References Cited

U.S. PATENT DOCUMENTS

| 556,421 A | 3/1896 | Judge |
| 4,200,110 A | 4/1980 | Peterson et al. |

(Continued)

FOREIGN PATENT DOCUMENTS

| EP | 2967333 | 1/2016 |
| EP | 3440999 | 2/2019 |

(Continued)

OTHER PUBLICATIONS

Extended European Search Report for European Patent Application No. 18207668.7 dated Apr. 3, 2019 (7 pages).
(Continued)

*Primary Examiner* — Eric F Winakur
(74) *Attorney, Agent, or Firm* — Pauly, DeVries Smith & Deffner LLC

(57) ABSTRACT

Embodiments herein relate to optoelectronic interfaces for multimode analyte sensors for use with implantable medical devices. In an embodiment, an implantable medical device is included. The implantable medical device can include a first chemical sensor including an optical excitation assembly comprising a first visible spectrum emitter, a second visible spectrum emitter, and at least one of a near-infrared (NIR) emitter and an ultraviolet emitter. The first chemical sensor can also include an optical detection assembly including a colorimetric response detector, and a photoluminescent response detector. The first chemical sensor can also include a multimode sensing element including a colorimetric response element specific for a first chemical analyte, a photoluminescent response element specific for a second chemical analyte. Other embodiments are also included herein.

20 Claims, 7 Drawing Sheets

(51) Int. Cl.

| | |
|---|---|
| *G01J 3/46* | (2006.01) |
| *G01J 3/28* | (2006.01) |
| *G01J 3/42* | (2006.01) |
| *G01J 3/51* | (2006.01) |
| *G01J 3/02* | (2006.01) |
| *A61B 5/145* | (2006.01) |
| *G01J 3/50* | (2006.01) |
| *A61B 5/1459* | (2006.01) |
| *G01J 3/44* | (2006.01) |

(52) U.S. Cl.
CPC ........... *G01J 3/0202* (2013.01); *G01J 3/0256* (2013.01); *G01J 3/0291* (2013.01); *G01J 3/28* (2013.01); *G01J 3/42* (2013.01); *G01J 3/4406* (2013.01); *G01J 3/46* (2013.01); *G01J 3/501* (2013.01); *G01J 3/513* (2013.01); *G01N 21/63* (2013.01); *A61B 5/0031* (2013.01); *A61B 5/0071* (2013.01); *A61B 5/14532* (2013.01)

(56) References Cited

U.S. PATENT DOCUMENTS

| | | | |
|---|---|---|---|
| 4,321,057 A | 3/1982 | Buckles | |
| 4,344,438 A | 8/1982 | Schultz | |
| 4,399,099 A | 8/1983 | Buckles | |
| 4,680,268 A | 7/1987 | Clark | |
| 4,704,029 A | 11/1987 | Van Heuvelen | |
| 4,721,677 A | 1/1988 | Clark | |
| 4,750,494 A | 6/1988 | King | |
| 4,750,495 A | 6/1988 | Moore et al. | |
| 4,890,621 A | 1/1990 | Hakky | |
| 4,903,701 A | 2/1990 | Moore | |
| 4,981,779 A | 1/1991 | Wagner | |
| 5,001,054 A | 3/1991 | Wagner | |
| 5,040,533 A | 8/1991 | Fearnot | |
| 5,090,326 A | 2/1992 | Altenau et al. | |
| 5,209,231 A | 5/1993 | Cote et al. | |
| 5,267,151 A | 11/1993 | Ham et al. | |
| 5,275,171 A | 1/1994 | Barcel | |
| 5,312,439 A | 5/1994 | Loeb | |
| 5,312,454 A | 5/1994 | Roline et al. | |
| 5,330,718 A | 7/1994 | Hui et al. | |
| 5,333,609 A | 8/1994 | Bedingham et al. | |
| 5,342,406 A | 8/1994 | Thompson | |
| 5,342,789 A | 8/1994 | Chick et al. | |
| 5,378,432 A | 1/1995 | Bankert et al. | |
| 5,419,329 A | 5/1995 | Smith et al. | |
| 5,457,535 A | 10/1995 | Schmidtke et al. | |
| 5,553,616 A | 9/1996 | Ham et al. | |
| 5,556,421 A | 9/1996 | Prutchi et al. | |
| 5,560,356 A | 10/1996 | Peyman | |
| 5,605,152 A | 2/1997 | Slate et al. | |
| 5,607,644 A | 3/1997 | Olstein et al. | |
| 5,660,163 A | 8/1997 | Schulman et al. | |
| 5,728,281 A | 3/1998 | Holmstrom et al. | |
| 5,730,125 A | 3/1998 | Prutchi et al. | |
| 5,797,898 A | 8/1998 | Santini et al. | |
| 5,830,138 A | 11/1998 | Wilson | |
| 5,833,603 A | 11/1998 | Kovacs et al. | |
| 5,854,078 A | 12/1998 | Asher | |
| 5,871,442 A | 2/1999 | Madarasz et al. | |
| 5,902,326 A | 5/1999 | Lessar et al. | |
| 5,958,782 A | 9/1999 | Bentsen et al. | |
| 5,995,860 A | 11/1999 | Sun et al. | |
| 6,002,954 A | 12/1999 | Van Antwerp et al. | |
| 6,011,984 A | 1/2000 | Van Antwerp et al. | |
| 6,040,194 A | 3/2000 | Chick et al. | |
| 6,049,727 A | 4/2000 | Crothall | |
| 6,070,093 A | 5/2000 | Oosta et al. | |
| 6,097,139 A | 8/2000 | Tuck et al. | |
| 6,122,536 A | 9/2000 | Sun et al. | |
| 6,123,861 A | 9/2000 | Santini et al. | |
| 6,125,290 A | 9/2000 | Miesel | |
| 6,125,291 A | 9/2000 | Miesel et al. | |
| 6,134,459 A | 10/2000 | Roberts et al. | |
| 6,144,866 A | 11/2000 | Miesel et al. | |
| 6,163,714 A | 12/2000 | Stanley et al. | |
| 6,175,642 B1 | 1/2001 | Gobbi et al. | |
| 6,187,599 B1 | 2/2001 | Asher et al. | |
| 6,216,022 B1 | 4/2001 | Tyrrell et al. | |
| 6,219,137 B1 | 4/2001 | Vo-Dinh | |
| 6,232,130 B1 | 5/2001 | Wolf | |
| 6,236,870 B1 | 5/2001 | Madarasz et al. | |
| 6,256,522 B1 | 7/2001 | Schultz | |
| 6,267,724 B1 | 7/2001 | Taylor | |
| 6,268,161 B1 | 7/2001 | Han et al. | |
| 6,277,627 B1 | 8/2001 | Hellinga | |
| 6,304,766 B1 | 10/2001 | Colvin, Jr. | |
| 6,330,464 B1 | 12/2001 | Colvin, Jr. et al. | |
| 6,343,223 B1 | 1/2002 | Chin et al. | |
| 6,344,340 B1 | 2/2002 | Dibner et al. | |
| 6,368,274 B1 | 4/2002 | Van Antwerp et al. | |
| 6,383,767 B1 | 5/2002 | Polak | |
| 6,438,397 B1 | 8/2002 | Bosquet et al. | |
| 6,442,409 B1 | 8/2002 | Peyman | |
| 6,454,710 B1 | 9/2002 | Ballerstadt et al. | |
| 6,466,821 B1 | 10/2002 | Pianca et al. | |
| 6,491,639 B1 | 12/2002 | Turcott | |
| 6,491,666 B1 | 12/2002 | Santini, Jr. et al. | |
| 6,505,059 B1 | 1/2003 | Kollias et al. | |
| 6,521,446 B2 | 2/2003 | Hellinga | |
| 6,527,762 B1 | 3/2003 | Santini, Jr. et al. | |
| 6,544,800 B2 | 4/2003 | Asher | |
| 6,551,838 B2 | 4/2003 | Santini, Jr. et al. | |
| 6,579,690 B1 | 6/2003 | Bonnecaze et al. | |
| 6,594,092 B2 | 7/2003 | Von et al. | |
| 6,594,510 B2 | 7/2003 | Madarasz et al. | |
| 6,602,521 B1 | 8/2003 | Ting et al. | |
| 6,625,479 B1 | 9/2003 | Weber et al. | |
| 6,666,821 B2 | 12/2003 | Keimel et al. | |
| 6,671,527 B2 | 12/2003 | Petersson et al. | |
| 6,673,596 B1 | 1/2004 | Sayler et al. | |
| 6,682,938 B1 | 1/2004 | Satcher, Jr. et al. | |
| 6,694,158 B2 | 2/2004 | Polak | |
| 6,711,423 B2 | 3/2004 | Colvin, Jr. | |
| 6,731,976 B2 | 5/2004 | Penn et al. | |
| RE38,525 E | 6/2004 | Stanley et al. | |
| 6,766,183 B2 | 7/2004 | Walsh et al. | |
| 6,771,993 B2 | 8/2004 | Rule et al. | |
| 6,800,451 B2 | 10/2004 | Daniloff et al. | |
| 6,804,544 B2 | 10/2004 | Van Antwerp et al. | |
| 6,814,490 B1 | 11/2004 | Suhm et al. | |
| 6,815,162 B2 | 11/2004 | Boukherroub et al. | |
| 6,835,553 B2 | 12/2004 | Han et al. | |
| 6,855,556 B2 | 2/2005 | Amiss et al. | |
| 6,875,208 B2 | 4/2005 | Santini, Jr. et al. | |
| 6,885,881 B2 | 4/2005 | Leonhardt | |
| 6,885,883 B2 | 4/2005 | Parris et al. | |
| 6,893,545 B2 | 5/2005 | Gotoh et al. | |
| 6,912,078 B2 | 6/2005 | Kudrle et al. | |
| 6,918,873 B1 | 7/2005 | Millar et al. | |
| 6,928,325 B2 | 8/2005 | Zhu et al. | |
| 6,937,900 B1 | 8/2005 | Pianca et al. | |
| 6,944,488 B2 | 9/2005 | Roberts | |
| 6,952,603 B2 | 10/2005 | Gerber et al. | |
| 6,957,094 B2 | 10/2005 | Chance et al. | |
| 6,976,982 B2 | 12/2005 | Santini, Jr. et al. | |
| 6,978,182 B2 | 12/2005 | Mazar et al. | |
| 7,016,714 B2 | 3/2006 | Colvin, Jr. et al. | |
| 7,039,446 B2 | 5/2006 | Ruchti et al. | |
| 7,070,590 B2 | 7/2006 | Santini, Jr. et al. | |
| 7,107,086 B2 | 9/2006 | Reihl et al. | |
| 7,133,710 B2 | 11/2006 | Acosta et al. | |
| 7,134,999 B2 | 11/2006 | Brauker et al. | |
| 7,164,948 B2 | 1/2007 | Struble et al. | |
| 7,166,871 B2 | 1/2007 | Erchak | |
| 7,174,212 B1 | 2/2007 | Klehn et al. | |
| 7,225,024 B2 | 5/2007 | Zhu et al. | |
| 7,236,821 B2 | 6/2007 | Cates et al. | |
| 7,410,616 B2 | 8/2008 | Santini, Jr. et al. | |
| 7,447,533 B1 | 11/2008 | Fang et al. | |
| 7,449,246 B2 | 11/2008 | Kim et al. | |
| 7,450,980 B2 | 11/2008 | Kawanishi | |

(56) References Cited

U.S. PATENT DOCUMENTS

| | | | |
|---|---|---|---|
| 7,471,290 B2 | 12/2008 | Wang et al. | |
| 7,577,470 B2 | 8/2009 | Shah et al. | |
| 7,632,234 B2 | 12/2009 | Manda et al. | |
| 7,633,356 B2 | 12/2009 | Hamet et al. | |
| 7,686,762 B1 | 3/2010 | Najafi et al. | |
| 7,761,130 B2 | 7/2010 | Simpson et al. | |
| 7,805,174 B2 | 9/2010 | Carpenter et al. | |
| 7,809,441 B2 | 10/2010 | Kane et al. | |
| 7,829,147 B2 | 11/2010 | Aitken et al. | |
| 7,890,171 B2 | 2/2011 | Zhu et al. | |
| 7,894,884 B2 | 2/2011 | Song et al. | |
| 8,126,554 B2 | 2/2012 | Kane et al. | |
| 8,131,364 B2 | 3/2012 | Zhu et al. | |
| 8,141,489 B2 | 3/2012 | Belanger et al. | |
| 8,160,670 B2 | 4/2012 | Ouyang et al. | |
| 8,165,840 B2 | 4/2012 | Hatlestad et al. | |
| 8,257,067 B2 | 9/2012 | Fukui et al. | |
| 8,290,592 B2 | 10/2012 | Michael et al. | |
| 8,303,511 B2 | 11/2012 | Eigler et al. | |
| 8,378,453 B2 | 2/2013 | Fedorov et al. | |
| 8,414,489 B2 | 4/2013 | Shah et al. | |
| 8,435,604 B2 | 5/2013 | Aitken et al. | |
| 8,527,067 B2 | 9/2013 | De Kock et al. | |
| 8,571,659 B2 | 10/2013 | Kane et al. | |
| 8,710,625 B2 | 4/2014 | Fedorov et al. | |
| 8,827,899 B2 | 9/2014 | Farr et al. | |
| 9,101,277 B2 | 8/2015 | Doerr | |
| 9,357,968 B2 | 6/2016 | Hauer et al. | |
| 9,693,714 B2 * | 7/2017 | DeHennis | A61B 5/1455 |
| 2002/0016535 A1 | 2/2002 | Martin et al. | |
| 2002/0026108 A1 | 2/2002 | Colvin | |
| 2002/0033260 A1 | 3/2002 | Lungwitz et al. | |
| 2002/0033454 A1 | 3/2002 | Cheng et al. | |
| 2002/0035317 A1 | 3/2002 | Cheng et al. | |
| 2002/0095075 A1 | 7/2002 | Madarasz et al. | |
| 2002/0127626 A1 | 9/2002 | Daniloff et al. | |
| 2003/0100040 A1 | 5/2003 | Bonnecaze et al. | |
| 2003/0114735 A1 | 6/2003 | Silver et al. | |
| 2003/0191376 A1 | 10/2003 | Samuels et al. | |
| 2003/0208113 A1 | 11/2003 | Mault et al. | |
| 2004/0023317 A1 | 2/2004 | Motamedi et al. | |
| 2004/0030365 A1 | 2/2004 | Rubin | |
| 2004/0059206 A1 | 3/2004 | Braig et al. | |
| 2004/0073100 A1 | 4/2004 | Ballerstadt et al. | |
| 2004/0087842 A1 | 5/2004 | Lakowicz et al. | |
| 2004/0100376 A1 | 5/2004 | Lye et al. | |
| 2004/0106953 A1 | 6/2004 | Yomtov et al. | |
| 2004/0132172 A1 | 7/2004 | Cunningham et al. | |
| 2004/0133079 A1 | 7/2004 | Mazar et al. | |
| 2004/0147034 A1 | 7/2004 | Gore et al. | |
| 2004/0161853 A1 | 8/2004 | Yang et al. | |
| 2004/0176669 A1 | 9/2004 | Colvin, Jr. | |
| 2004/0180379 A1 | 9/2004 | Van Duyne et al. | |
| 2004/0180391 A1 | 9/2004 | Gratzl et al. | |
| 2004/0186359 A1 | 9/2004 | Beaudoin et al. | |
| 2004/0199062 A1 | 10/2004 | Petersson et al. | |
| 2004/0206916 A1 | 10/2004 | Colvin, Jr. et al. | |
| 2004/0215134 A1 | 10/2004 | Soykan et al. | |
| 2004/0249311 A1 | 12/2004 | Haar et al. | |
| 2004/0254438 A1 | 12/2004 | Chuck et al. | |
| 2004/0260162 A1 | 12/2004 | Rohleder et al. | |
| 2005/0027176 A1 | 2/2005 | Xie | |
| 2005/0033133 A1 | 2/2005 | Kraft | |
| 2005/0038329 A1 | 2/2005 | Morris et al. | |
| 2005/0042704 A1 | 2/2005 | Alarcon et al. | |
| 2005/0043894 A1 | 2/2005 | Fernandez | |
| 2005/0065464 A1 | 3/2005 | Talbot et al. | |
| 2005/0065556 A1 | 3/2005 | Reghabi et al. | |
| 2005/0070768 A1 | 3/2005 | Zhu et al. | |
| 2005/0070770 A1 | 3/2005 | Dirac et al. | |
| 2005/0070771 A1 | 3/2005 | Rule et al. | |
| 2005/0096587 A1 | 5/2005 | Santini et al. | |
| 2005/0113657 A1 | 5/2005 | Alarcon et al. | |
| 2005/0113658 A1 | 5/2005 | Jacobson et al. | |
| 2005/0130249 A1 | 6/2005 | Parris et al. | |
| 2005/0137481 A1 | 6/2005 | Sheard et al. | |
| 2005/0148832 A1 | 7/2005 | Reghabi et al. | |
| 2005/0149139 A1 | 7/2005 | Plicchi et al. | |
| 2005/0154272 A1 | 7/2005 | Dirac et al. | |
| 2005/0221276 A1 | 10/2005 | Rozakis et al. | |
| 2005/0221277 A1 | 10/2005 | Kawanishi | |
| 2005/0228226 A1 | 10/2005 | Muckner | |
| 2006/0025748 A1 | 2/2006 | Ye | |
| 2006/0076236 A1 | 4/2006 | Shah et al. | |
| 2006/0217771 A1 | 9/2006 | Soykan et al. | |
| 2006/0229694 A1 | 10/2006 | Schulman et al. | |
| 2007/0027495 A1 | 2/2007 | Gerber | |
| 2007/0118056 A1 | 5/2007 | Wang et al. | |
| 2007/0219628 A1 | 9/2007 | Shanley et al. | |
| 2007/0252713 A1 | 11/2007 | Rondoni et al. | |
| 2007/0270674 A1 | 11/2007 | Kane et al. | |
| 2007/0270675 A1 | 11/2007 | Kane et al. | |
| 2007/0275035 A1 | 11/2007 | Herman et al. | |
| 2008/0033260 A1 | 2/2008 | Sheppard et al. | |
| 2008/0046080 A1 | 2/2008 | Vanden et al. | |
| 2008/0077190 A1 | 3/2008 | Kane | |
| 2008/0082001 A1 | 4/2008 | Hatlestad et al. | |
| 2008/0152283 A1 | 6/2008 | Nielsen et al. | |
| 2008/0294209 A1 | 11/2008 | Thompson et al. | |
| 2009/0018425 A1 | 1/2009 | Ouyang et al. | |
| 2009/0024045 A1 | 1/2009 | Prakash et al. | |
| 2009/0076353 A1 | 3/2009 | Carpenter et al. | |
| 2009/0124875 A1 | 5/2009 | Bentsen et al. | |
| 2009/0221885 A1 | 9/2009 | Hall et al. | |
| 2009/0312973 A1 | 12/2009 | Hatlestad et al. | |
| 2010/0057057 A1 | 3/2010 | Hayter et al. | |
| 2010/0149544 A1 | 6/2010 | Ghislain | |
| 2010/0280578 A1 | 11/2010 | Skelton et al. | |
| 2011/0024307 A1 | 2/2011 | Simpson et al. | |
| 2011/0130666 A1 | 6/2011 | Dong et al. | |
| 2013/0060105 A1 | 3/2013 | Shah et al. | |
| 2013/0150689 A1 | 6/2013 | Shaw-klein | |
| 2013/0184599 A1 | 7/2013 | Friedman et al. | |
| 2013/0197332 A1 | 8/2013 | Lucisano et al. | |
| 2014/0091945 A1 | 4/2014 | Rivas et al. | |
| 2014/0155710 A1 | 6/2014 | Rowland et al. | |
| 2014/0276164 A1 | 9/2014 | Thakur et al. | |
| 2014/0286875 A1 * | 9/2014 | Gamsey | A61B 5/14532 424/9.61 |
| 2014/0357964 A1 | 12/2014 | Wisniewski et al. | |
| 2014/0364758 A1 | 12/2014 | Schindhelm et al. | |
| 2015/0057509 A1 | 2/2015 | Huffstetler et al. | |
| 2015/0164383 A1 | 6/2015 | Varsavsky et al. | |
| 2015/0352229 A1 | 12/2015 | Brill et al. | |
| 2016/0363550 A1 | 12/2016 | Koo et al. | |
| 2016/0374597 A1 | 12/2016 | Stahmann | |
| 2017/0215732 A1 | 8/2017 | Genier et al. | |
| 2017/0245788 A1 | 8/2017 | Heikenfeld | |
| 2018/0153451 A1 | 6/2018 | Heikenfeld et al. | |
| 2018/0344218 A1 | 12/2018 | Li et al. | |
| 2019/0029567 A1 | 1/2019 | Stahmann et al. | |
| 2019/0046032 A1 | 2/2019 | Stahmann et al. | |
| 2019/0059792 A1 | 2/2019 | Kane et al. | |
| 2019/0125228 A1 | 5/2019 | Kane et al. | |
| 2019/0167162 A1 | 6/2019 | Li et al. | |

FOREIGN PATENT DOCUMENTS

| | | |
|---|---|---|
| JP | 2005287762 | 10/2005 |
| JP | 2005315871 | 11/2005 |
| JP | 2006507078 | 3/2006 |
| JP | 2006126715 | 5/2006 |
| JP | 2007525858 | 9/2007 |
| JP | 2009537247 | 10/2009 |
| WO | 9625978 | 8/1996 |
| WO | 9719188 | 5/1997 |
| WO | 9801071 | 1/1998 |
| WO | 9902651 | 1/1999 |
| WO | 0018289 | 4/2000 |
| WO | 0025862 | 5/2000 |
| WO | 0025863 | 5/2000 |
| WO | 0180728 | 11/2001 |
| WO | 2004039265 | 5/2004 |
| WO | 2004071291 | 8/2004 |

(56) References Cited

FOREIGN PATENT DOCUMENTS

| WO | 2004081522 | 9/2004 |
|---|---|---|
| WO | 2004091719 | 10/2004 |
| WO | 2004092713 | 10/2004 |
| WO | 2005074612 | 8/2005 |
| WO | 2006017169 | 2/2006 |
| WO | 2007110867 | 10/2007 |
| WO | 2007137037 | 11/2007 |
| WO | 2009038996 | 3/2009 |
| WO | 2013016573 | 1/2013 |
| WO | 2015048514 | 4/2015 |
| WO | 2019023093 | 1/2019 |
| WO | 2019040635 | 2/2019 |

OTHER PUBLICATIONS

"Extended European Search Report," for European Patent Application No. 18209525.7 dated Feb. 27, 2019 (12 pages).
"International Search Report and Written Opinion," for PCT Application No. PCT/US2018/043225 dated Nov. 16, 2018 (11 pages).
"Partial European Search Report," for European Patent Application No. 18188253.1 dated Jan. 7, 2019 (11 pages).
Anderson, J. M. et al., "Monocyte, Macrophage and foreign body giant cell interactions with molecularly engineered surfaces," Journal of Materials Science: Materials in Medicine 10 (1999) 579-588 (10 pages).
Anderson, James M. "Biological Responses to Materials," Annu. Rev. Mater. Res. 2001. 31:81-110 (30 pages).
Anderson, James M. et al., "Foreign Body Reaction to Biomaterials," Semin. Immunol. Apr. 2008; 20(2): 86-100 (27 pages).
Bakker, Eric et al., "Carrier-Based Ion-Selective Electrodes and Bulk Optodes. 1. General Characteristics," Chem. Rev. 1997, 97, 3083-3132 (50 pages).
Benco, John S. et al., "Optical Sensors for Blood Analytes," The Spectrum, vol. 14, Issue 4, pp. 4-11, Winter 2001 (8 pages).
Bender, J. W. et al., "The Use of Biomedical Sensors to Monitor Capsule Formation Around Soft Tissue Implants," Annals of Plastic Surgery, vol. 56, No. 1, Jan. 2006, pp. 72-77 (6 pages).
Bridges, Amanda W. et al., "Anti-Inflammatory Polymeric Coatings for Implantable Biomaterials and Devices," Journal of Diabetes Science and Technology 2008;2(6):984-994 (11 pages).
Buhlmann, Philippe et al., "Carrier-Based Ion-Selective Electrodes and Bulk Optodes. 2. Ionophores for Potentiometric and Optical Sensors," Chem. Rev. 1998, 98, 1593-1687 (95 pages).
"Communication Pursuant to Article 94(3) EPC," for European Patent Application No. 07762189.4 dated Mar. 24, 2009 (3 pages).
"Communication pursuant to Article 94(3) EPC," for European Patent Application No. 07762189.4 dated Mar. 16, 2010 (3 pages).
"Extended European Search Report," for European Patent Application No. 18174561.3 dated Aug. 28, 2018 (9 pages).
File History for U.S. Appl. No. 11/383,926.
File History for U.S. Appl. No. 11/383,933.
File History for U.S. Patent Application No. 11/856,850.
File History for U.S. Appl. No. 12/391,761.
"First Examination Report," for Australian Patent Application No. 2008302499 dated Feb. 8, 2011 (1 page).
Han, In S. et al., "Constant-Volume Hydrogel Osmometer: A New Device Concept for Miniature Biosensors," Biomacromolecules, 3 2002, pp. 1271-1275 (5 pages).
He, Huarui et al., "Enantioselective Optodes," Analytica Chimica Acta, 246, pp. 251-257, 1991 (7 pages).
He, Wei et al., "A Novel Anti-inflammatory Surface for Neural Electrodes," Adv. Mater. 2007, 19, 3529-3533 (5 pages).
Helton, Kristen L. et al., "Biomechanics of the Sensor-Tissue Interface-Effects of Motion, Pressure, and Design on Sensor Performance and the Foreign Body Response—Part I: Theoretical Framework," Journal of Diabetes Science and Technology 2011;5(3):632-646 (15 pages).
"International Preliminary Report on Patentability," for PCT Application No. PCT/US2008/075673 dated Mar. 24, 2010 (6 pages).

"International Search Report and Written Opinion," for PCT Application No. PCT/US2008/075673 dated Nov. 28, 2008 (13 pages).
Koh, Ahyeon et al., "Glucose Sensor Membranes for Mitigating the Foreign Body Response," Journal of Diabetes Science and Technology 2011;5(5):1052-1059 (8 pages).
Koronczi, et al., "Development of a submicron optochemical potassium sensor with enhanced stability due to internal reference," Sensors and Actuators B, 51:188-195 (1998).
Kuwana, Eddy et al., "Sensing of pH in Multiply Scattering Media with Fluorescence Lifetime," Advanced Biomedical and Clinical Diagnostic Systems, Proceedings of SPIE, vol. 4958, pp. 32-42, 2003 (11 pages).
Lehn, J. M. et al., "[2]-Cryptates: Stability and Selectivity of Alkali and Akaline-Earth Macrobicycle Complexes," Journal of the American Chemical Society, Nov. 12, 1975 pp. 6700-6707 (8 pages).
Lima-Oliveira, Gabriel et al., "Patient Posture for Blood Collection by Venipuncture: Recall for Standardization After 28 Years," Brazilian Journal of Hematology and Hemotherapy 2017 <http://dx.doi.org/10.1016/j.bjhh.2017.01.004> (6 pages).
Messier, "The Joining of Materials," Nov. 2004 (58 pages).
"Microminiature Device Monitors Vital Electrolytes and Metabolites," John Glenn Biomedical Engineering Consortium, May 2002 (2 pages).
"Microminiature Monitor for Vital Electrolyte and Metabolite Levels of Astronauts—Status Report," John Glenn Biomedical Engineering Consortium NASA Glenn Research Center at Lewis Field, Apr. 2003 (5 pages). NASA Glenn Research Center at Lewis Field.
Novak, Matthew T. et al., "Modeling the relative impact of capsular tissue effects on implanted glucose sensor time lag and signal attenuation," Anal. Bioanal. Chem. Oct. 2010; 398(4):1695-1705 (22 pages).
"Office Action," for Japanese Patent Application No. 2010-524940 dated Nov. 22, 2011 (8 pages) with English translation.
Padmanabhan, Jagnnath et al., "Nanomaterials, Inflammation and Tissue Engineering," Wiley Interdiscip Rev Nanomed Nanobiotechnol. May 2015; 7(3):355-370 (23 pages).
"PCT International Search Report and Written Opinion," for International Application No. PCT/US2007/068954, dated Nov. 17, 2008 (12 pages).
"Response to Communication Pursuant to Article 94(3) EPC," for European Patent Application No. 07762189.4 filed with the EPO Jul. 27, 2009 (8 pages).
Roger, Yvonne et al., "Grid-like surface structures in thermoplastic polyurethane induce anti-inflammatory and anti-fibrotic processes in bone marrow-derived mesenchymal stem cells," Abstract Only Colloids and Surfaces B: Biointerfaces vol. 148, Dec. 2016, pp. 104-115 (4 pages).
Seelig, Mildred S. "Electrographic Patterns of Magnesium Depletion Appearing in Alcoholic Heart Disease," Annals of the New York Academy of Sciences, vol. 162, Article 2, 1969, pp. 906-917 (13 pages).
Sharkawy, A. A. et al., "Engineering the tissue which encapsulates subcutaneous implants. I. Diffusion properties," Department of Biomedical Engineering, NSF Center for Emerging Cardiovascular Technology, Duke University, Durham, North Carolina 1996 (12 pages).
Shirreffs, S. M. "The Effect of Posture Change on Blood Volume, Serum Potassium, and Whole Body Electrical Impedance," Eur. J. Appl. Physiol. (1994)69:461-463 (3 pages).
Tohda, Koji et al., "A Microscopic, Continuous, Optical Monitor for Interstitial Electrolytes and Glucose," Chemphyschem 2003, pp. 155-160 (6 pages).
Tohda, Koji et al., "Micro-miniature Autonomous Optical Sensor Array for Monitoring Ions and Metabolites 1: Design, Fabrication, and Data Analysis," Analytical Sciences, Mar. 2006, vol. 22 pp. 383-388 (6 pages).
Tsai, Hc et al., "Simultaneous Determination of Renal Clinical Analytes in Serum using Hydrolase- and Oxidase-Encapsulated Optical Array Biosensors," Analytical Biochemistry 334 (2004) 183-192 (10 pages).
"Upconverting nanoparticles," Wikipeda.com accessed Jun. 12, 2017 (13 pages).

(56) References Cited

OTHER PUBLICATIONS

Voskerician, Gabriela et al., "Biocompatibility and Biofouling of MEMs Drug Delivery Devices," Biomaterials 24 (2003) 1959-1967 (9 pages).
Weisberg, Lawrence S. "Management of Severe Hyperkalemia," Crit Care Med 2008 vol. 36, No. 12 (6 pages).
International Search Report and Written Opinion for PCT Application No. PCT/US2018/047549 dated Oct. 26, 2018 (15 pages).
Extended European Search Report for European Patent Application No. 18202201.2 dated Jun. 28, 2019 (9 pages).
Response to Communication Pursuant to Rule 69 EPC for European Patent Application No. 18174561.3 filed Jun. 3, 2019 (21 pages).
Communication Pursuant to Article 94(3) EPC for European Patent Application No. 18174561.3 dated Jan. 27, 2020 (5 pages).
International Preliminary Report on Patentability for PCT Application No. PCT/US2018/043225 dated Feb. 6, 2020 (7 pages).
International Preliminary Report on Patentability for PCT Application No. PCT/US2018/047549 dated Mar. 5, 2020 (11 pages).
Response to Communication Pursuant to Rule 69 EPC for European Patent Application No. 18202201.2 filed Jan. 31, 2020 (22 pages).
Response to Communication Pursuant to Rule 69 EPC for European Patent Application No. 18209525.7 filed with the EPO Dec. 12, 2019 (33 pages).
Response to European Search Report for European Patent Application No. 18188253.1 filed Nov. 7, 2019 (14 pages).
Response to Extended European Search Report for European Patent Application No. 18207668.7 filed Nov. 29, 2019 (14 pages).
Communication Pursuant to Article 94(3) EPC for European Patent Application No. 18207668.7 dated Aug. 4, 2020 (5 pages).
Final Office Action for U.S. Appl. No. 15/992,823 dated Aug. 13, 2020 (18 pages).
Non-Final Office Action for U.S. Appl. No. 15/992,82 dated May 5, 2020 (51 pages).
Non-Final Office Action for U.S. Appl. No. 16/038,737 dated Jun. 22, 2020 (46 pages).
Non-Final Office Action for U.S. Appl. No. 16/041,923 dated Jul. 23, 2020 (61 pages).
Non-Final Office Action for U.S. Appl. No. 16/136,875 dated May 27, 2020 (43 pages).
Response to Non-Final Rejection dated May 27, 2020 for U.S. Appl. No. 16/136,875, submitted via EFS-Web on Jul. 22, 2020, 11 pages.
Response to Non-Final Rejection dated May 5, 2020 for U.S. Appl. No. 15/992,823, submitted via EFS-Web on Jul. 7, 2020, 10 pages.
Response to Communication Pursuant to Article 94(3) EPC for European Patent Application No. 18174561.3 filed Jul. 27, 2020 (11 pages).
Response to Non-Final Rejection dated Jun. 22, 2020 for U.S. Appl. No. 16/038,737, submitted via EFS-Web on Aug. 4, 2020, 10 pages.
Final Office Action for U.S. Appl. No. 16/136,875 dated Aug. 21, 2020 (10 pages).
Non-Final Office Action for U.S. Appl. No. 16/106,623 dated Oct. 9, 2020 (60 pages).
Response to Final Rejection dated Aug. 13, 2020 for U.S. Appl. No. 15/992,823, submitted via EFS-Web on Oct. 13, 2020, 9 pages.
Response to Final Rejection dated Aug. 21, 2020 for U.S. Appl. No. 16/136,875, submitted via EFS-Web on Oct. 13, 2020, 12 pages.
Response to Non-Final Rejection dated Jul. 23, 2020 for U.S. Appl. No. 16/041,923, submitted via EFS-Web on Oct. 13, 2020, 12 pages.

* cited by examiner

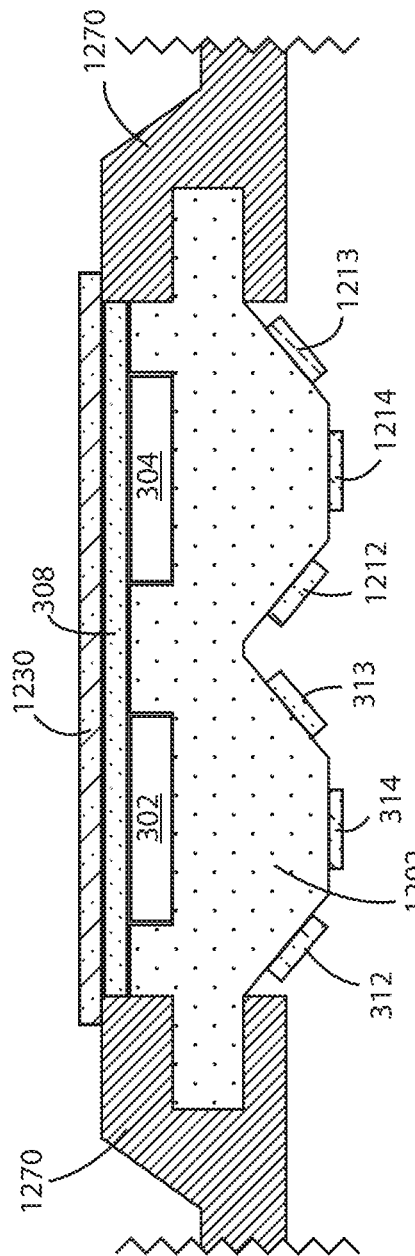
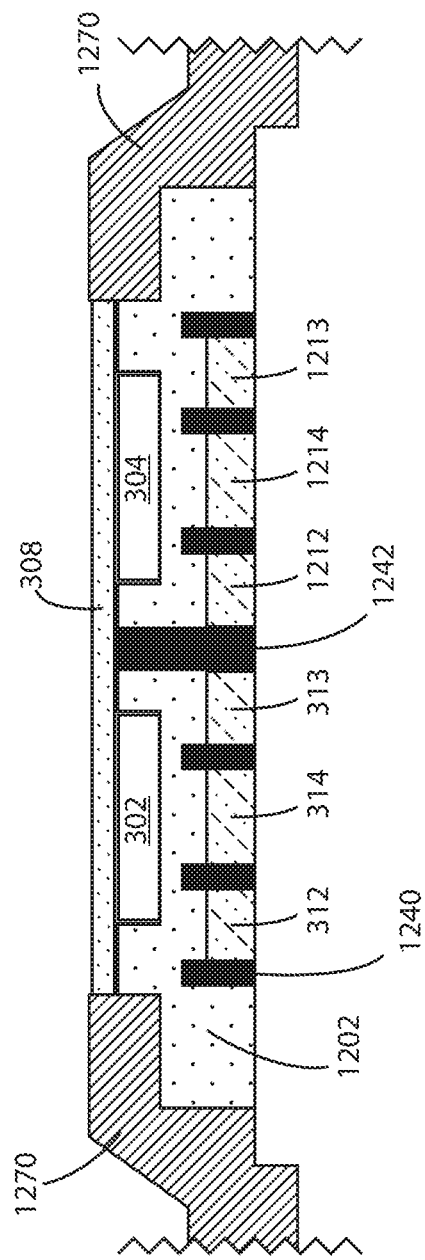
FIG. 12
FIG. 13

MULTIMODAL ANALYTE SENSOR OPTOELECTRONIC INTERFACE

This application claims the benefit of China Patent Application No. 2017/11266579.6 filed Dec. 5, 2017, the content of which is herein incorporated by reference in its entirety.

FIELD

Embodiments herein relate to multimode analyte sensors. In particular, embodiments herein relate to optoelectronic interfaces for multimode analyte sensors for use with implantable medical devices.

BACKGROUND

In the context of diagnosis and monitoring of patients, clinicians frequently evaluate many different pieces of data about their patients including physical observations, descriptions of symptoms, test results, and the like. One aspect that testing can reveal is the physiological concentration of chemical analytes such as electrolytes for the patient. Chemical analyte concentrations can be important to know because of their effect on various organs and bodily functions. In many cases, chemical analyte concentrations are assessed by drawing a fluid sample (or other sample) from the patient followed by an in vitro assay.

SUMMARY

Embodiments herein relate to optoelectronic interfaces for multimode analyte sensors for use with implantable medical devices. In a first aspect, an implantable medical device is included. The implantable medical device can include a first chemical sensor including an optical excitation assembly comprising a first visible spectrum emitter, a second visible spectrum emitter, and at least one of a near-infrared (NIR) emitter and an ultraviolet emitter. The first chemical sensor can also include an optical detection assembly including a colorimetric response detector, and a photoluminescent response detector. The first chemical sensor can also include a multimode sensing element including a colorimetric response element specific for a first chemical analyte, a photoluminescent response element specific for a second chemical analyte.

In a second aspect, in addition to one or more of the preceding or following aspects, or in the alternative to some aspects, a low-pass optical filter disposed over or in the photoluminescent response detector can be included.

In a third aspect, in addition to one or more of the preceding or following aspects, or in the alternative to some aspects, the colorimetric response detector and the photoluminescent response detector can be integrated as a single unit.

In a fourth aspect, in addition to one or more of the preceding or following aspects, or in the alternative to some aspects, the colorimetric response detector and the photoluminescent response detector can be separate units.

In a fifth aspect, in addition to one or more of the preceding or following aspects, or in the alternative to some aspects, the multimode sensing element can include an outer barrier layer forming a top, a bottom, and opposed sides of the sensing element; the outer barrier layer defining an interior volume. The colorimetric response element and the photoluminescent response element can both be disposed throughout the interior volume.

In a sixth aspect, in addition to one or more of the preceding or following aspects, or in the alternative to some aspects, the top of the outer barrier layer can include an analyte window.

In a seventh aspect, in addition to one or more of the preceding or following aspects, or in the alternative to some aspects, the analyte window is opaque to the passage of light.

In an eighth aspect, in addition to one or more of the preceding or following aspects, or in the alternative to some aspects, the multimode sensing element can include an outer barrier layer forming a top, a bottom, and opposed sides of the sensing element. The outer barrier layer can define an interior volume and polymeric beads can be disposed within the interior volume. The colorimetric response element and the photoluminescent response element can both be disposed on or within the polymeric beads.

In a ninth aspect, in addition to one or more of the preceding or following aspects, or in the alternative to some aspects, a second chemical sensor can be included. The second chemical sensor can include an optical excitation assembly including a first visible spectrum emitter, a second visible spectrum emitter, and at least one of a near-infrared (NIR) emitter and an ultraviolet emitter. The second chemical sensor can include an optical detection assembly comprising a colorimetric response detector and a photoluminescent response detector. The second chemical sensor can also include a multimode sensing element including a colorimetric response element specific for a third chemical analyte and a photoluminescent response element specific for a fourth chemical analyte.

In a tenth aspect, in addition to one or more of the preceding or following aspects, or in the alternative to some aspects, a housing can be included and a circuit board can be disposed within the housing, the housing having a top surface and a bottom surface, the multimode sensing element disposed on or within the top surface.

In an eleventh aspect, in addition to one or more of the preceding or following aspects, or in the alternative to some aspects, an electrode can be disposed on or within the bottom surface of the housing.

In a twelfth aspect, in addition to one or more of the preceding or following aspects, or in the alternative to some aspects, the circuit board can have a U-shaped portion and an overlapping portion adjacent to the U-shaped portion that overlaps other portions of the circuit board, the electrode attached to the overlapping portion.

In a thirteenth aspect, in addition to one or more of the preceding or following aspects, or in the alternative to some aspects, the housing can be a translucent epoxy.

In a fourteenth aspect, in addition to one or more of the preceding or following aspects, or in the alternative to some aspects, the circuit board can include side wings angled upward, and at least one of the first visible spectrum emitter, the second visible spectrum emitter, the near-infrared (NIR) emitter and the ultraviolet emitter can be disposed on a top surface of at least one side wing and pointed inward.

In a fifteenth aspect, in addition to one or more of the preceding or following aspects, or in the alternative to some aspects, at least one of the first visible spectrum emitter, the second visible spectrum emitter, the near-infrared (NIR) emitter and the ultraviolet emitter are disposed on a top surface of at least one side wing and pointed inward at an angle of 5 to 60 degrees with respect to a plane perpendicular to a middle portion of the circuit board.

In a sixteenth aspect, in addition to one or more of the preceding or following aspects, or in the alternative to some aspects, a translucent optical body member is included and the multimode sensing element is disposed on or within a top side of the translucent optical body member and the optical excitation assembly and the optical detection assembly are disposed on or within a bottom side of the translucent optical body member.

In a seventeenth aspect, in addition to one or more of the preceding or following aspects, or in the alternative to some aspects, the bottom side of the translucent optical body member includes one or more flat portions and one or more angled portions and the optical excitation assembly is disposed at least partially on the one or more angled portions and the optical detection assembly is disposed at least partially on the one or more flat portions.

In an eighteenth aspect, in addition to one or more of the preceding or following aspects, or in the alternative to some aspects, the translucent optical body member includes a cured translucent adhesive material.

In a nineteenth aspect, in addition to one or more of the preceding or following aspects, or in the alternative to some aspects, the translucent optical body member includes a translucent polymer material.

In a twentieth aspect, in addition to one or more of the preceding or following aspects, or in the alternative to some aspects, a plurality of optical shrouds can be included and can be disposed between adjacent elements of the optical excitation assembly and/or optical detection assembly.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which:

FIG. 12 is a schematic cross-sectional view of a portion of an implantable medical device in accordance with various embodiments herein.

FIG. 13 is a schematic cross-sectional view of a portion of an implantable medical device in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Implantable analyte sensors can be used to gather data about physiological analytes while a patient is away from a medical care facility and without needing to draw blood or another fluid from the patient. The clinical value of data provided by implanted sensors increases (possibly exponentially) with the number of different analytes that can be observed simultaneously.

However, maximum device volume, complexity and surface area are severely constrained in the context of implanted devices. As such, the inclusion of additional sensors to increase the number of different analytes detected can negatively affect physical dimensions, circuit complexity, manufacturability, durability, yield and usability.

In accordance with embodiments herein, multimodal sensors (and in particular, chronically implanted multimodal sensors) can be used to detect multiple different analytes with each sensing element and thus allow for the detection of multiple different analytes without substantially increasing the overall complexity, size and power consumption of the device.

In various embodiments herein, implantable medical devices are equipped with multimodal analyte sensors. In particular, various analyte sensors herein can operate using both colorimetric sensing and photoluminescent sensing. Colorimetric sensing is accomplished using an indicator or moiety that changes its color upon binding with an analyte of interest and the resulting color change is then captured. Photoluminescent sensing (including, but not limited to, fluorescence and phosphorescence) operates very differently than colorimetry. Photoluminescent sensing is accomplished using an indicator or moiety that involves optical absorption and re-emission (typically at a longer wavelength) via a phosphor. Multimodal chemical (or analyte) sensors herein, such as bimodal sensors, can include both colorimetric sensing components and photoluminescent sensing components within the same sensing element such that the number of analytes can be multiplied without increasing the overall size and complexity of the device to the same degree that would otherwise be required if only unimodal analyte sensors were used.

Figure 1:
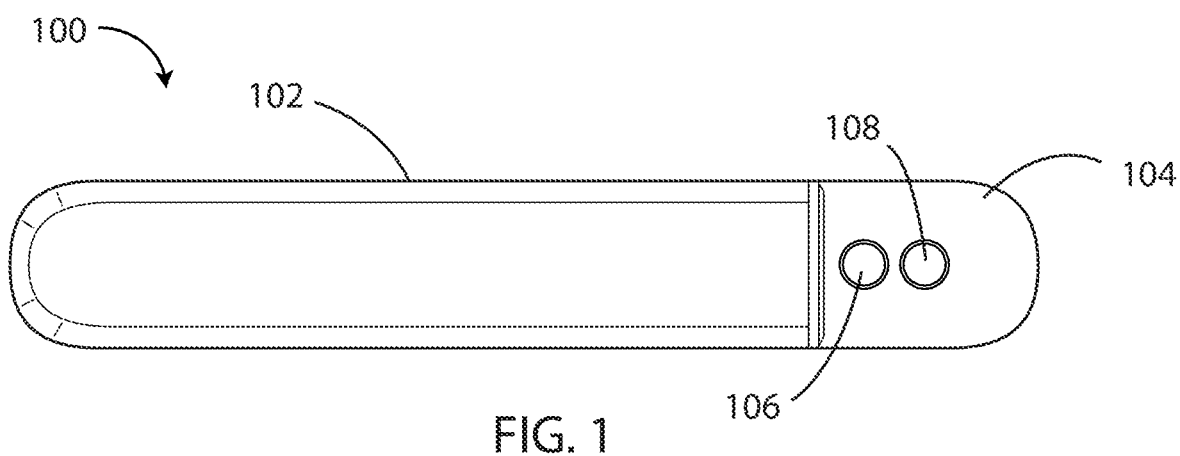
FIG. 1 is a schematic top view of an implantable medical device in accordance with various embodiments herein.

Referring now to FIG. 1, an implantable medical device (IMD) 100 is shown in accordance with the embodiments herein. The IMD 100 can include an implantable housing 102 and a header 104 coupled to the implantable housing 102. Various materials can be used. However, in some embodiments, the housing 102 can be formed of a material such as a metal, ceramic, a polymer, or a composite. The header 104 can be formed of various materials, but in some embodiments the header 104 can be formed of a polymer (translucent or opaque) such as an epoxy material. In some embodiments, the header 104 can be hollow. In other embodiments, the header 104 can be filled with components and/or structural materials such as epoxy or another material such that it is non-hollow.

The IMD 100 can also include analyte sensors 106 and 108 coupled to the implantable housing 102. Analyte sensors 106, 108 can each be configured to detect one or more analytes, such as an ion concentration of a bodily fluid, when implanted in the body. In various embodiments herein, analyte sensors 106, 108 are multimodal sensors as described more fully below. Bodily fluids can include blood, interstitial fluid, serum, lymph, serous fluid, cerebrospinal fluid, and the like.

In some embodiments, analyte sensors 106, 108 can each be configured to detect two or more analytes selected from ions, electrolytes, proteins, sugars, hormones, peptides, amino acids, metabolic products or the like. In some embodiments, the analyte sensors 106, 108 can be configured to detect an ion selected from the group consisting of potassium, sodium, calcium, magnesium, lithium, hydronium, hydrogen phosphate, chloride, bicarbonate, and the like. In some embodiments, the sensors 106, 108 can be configured to detect creatinine or glucose. However, many other physiological analytes are also contemplated herein and are discussed further below.

It will be appreciated that the analyte sensors 106, 108 can be positioned at any location along IMD 100, including along the implantable housing 102 and along the header 104. It will also be appreciated that though FIG. 1 shows a device having two multimodal analyte sensors 106, 108, any number of analyte sensors can be present. For example, the device can include at least 1, 2, 3, 4, 5, 6, 7, 8, 9, 10, 11, 12, or more analyte sensors, or a number of sensors falling within a range between any of the foregoing. In some embodiments the analyte sensors 106, 108 can be configured to detect the same analyte or same two analytes, whereas in other embodiments, the analyte sensors 106, 108 can be configured to detect different analytes.

The IMB 100 can take on various dimensions. In a particular embodiment herein, the IMB 100 can be approximately 2 to 3 inches in length, 0.4 to 0.6 inches wide, and 0.15 to 0.35 inches thick. However, in some embodiments, the IMB 100 can be about 0.25, 0.5, 1.0, 2.0, 3.0, 4.0, or 5.0 inches in length. In some embodiments, the length can be in a range wherein any of the foregoing lengths can serve as the upper or lower bound of the range, provided that the upper bound is greater than the lower bound. In some embodiments, the IMB 100 can be about 0.25, 0.5, 0.75, 1.0, or 2.0 inches in width. In some embodiments, the length can be in a range wherein any of the foregoing widths can serve as the upper or lower bound of the range, provided that the upper bound is greater than the lower bound. In some embodiments, the IMD 100 can be about 0.10, 0.25, 0.50, 0.75 or 1.0 inches thick. In some embodiments, the thickness can be in a range wherein any of the foregoing thicknesses can serve as the upper or lower bound of the range, provided that the upper bound is greater than the lower bound.

Figure 2:
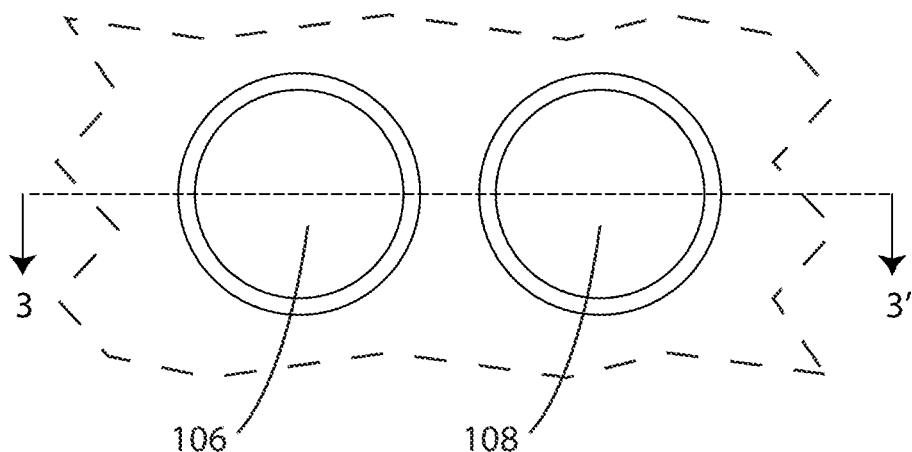
FIG. 2 is a schematic view of analyte sensors in accordance with various embodiments herein.

Referring now to FIG. 2, a top-down view of the analyte sensors 106, 108 is shown magnified with respect to FIG. 1. Analyte sensors 106, 108 are shown as circles, however, it will be appreciated that the analyte sensors embodied herein can take on many geometric shapes and sizes, including but not limited to squares, ovals, triangles, rectangles, pentagons, octagons, parallelograms, etc.

Figure 3:
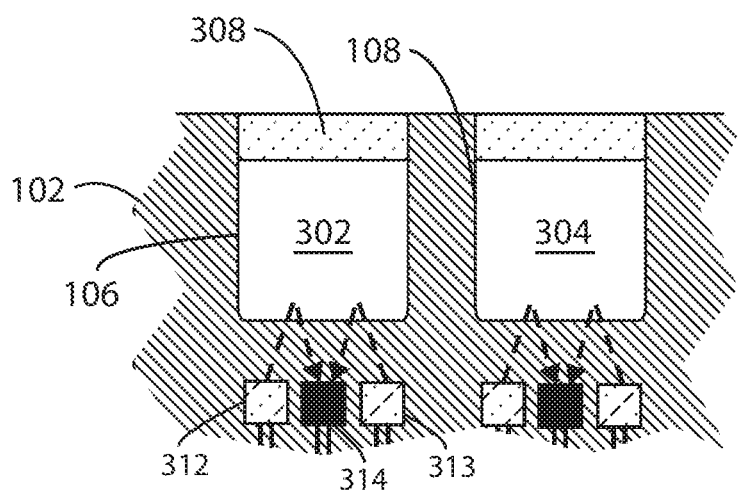
FIG. 3 is a cross-sectional view of analyte sensors taken along line 3-3' of FIG. 2.

Referring now to FIG. 3, a cross-sectional view of analyte sensors 106, 108 along line 3-3' of FIG. 2 is shown. Analyte sensors 106 and 108 can include, but are not limited to, sensing elements 302 and 304, respectively. Each of the analyte sensors 106, 108 can also include an analyte diffusion window 308 (or simply analyte window) disposed at the top of sensing elements 302, 304.

Each analyte window 308 can be formed from a permeable material, such as an ion permeable polymeric matrix material. Many different materials can be used as the ion permeable polymeric matrix material. In some embodiments, the ion permeable polymeric matrix material can be a hydrogel. In some embodiments, the ion permeable polymeric matrix material can be polyhydroxyethyl methacrylate (polyHEMA) either as a homopolymer or a copolymer including the same. The ion permeable polymeric matrix material(s) can be chosen based on its permeability to one or more of an electrolyte, a protein, a sugar, a hormone, a peptide, an amino acid, or a metabolic product. Specific ion permeable polymeric matrix material are discussed in more detail below. In some embodiments, the analyte window 308 can be opaque to the passage of light in one or more of the visible, ultraviolet (UV), or near-infrared (NIR) frequency spectrums.

FIG. 3 shows analyte sensors 106, 108 as optical analyte sensors. The optical analyte sensors can include optical excitation assemblies 312, 313 and optical detection 314 assemblies. Suitable optical excitation and optical detection assemblies for use herein are discussed in more detail below.

Figure 4:
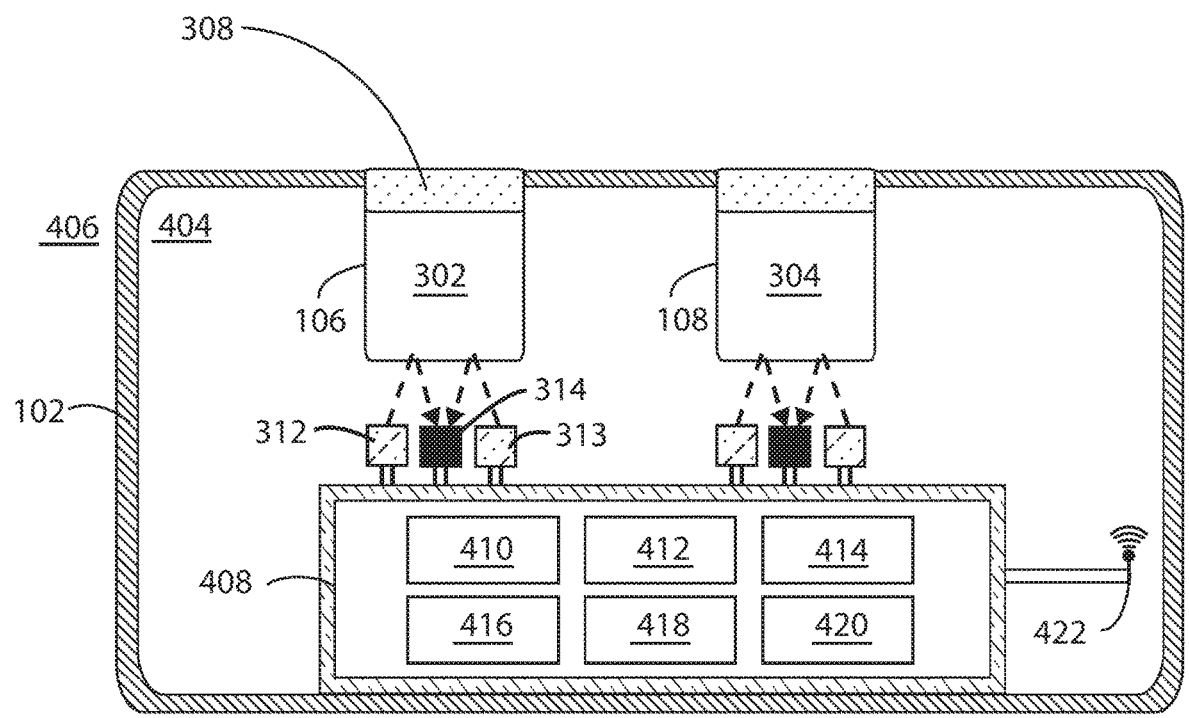
FIG. 4 is a schematic cross-sectional view of an implantable medical device in accordance with various embodiments herein.
Figure 6:
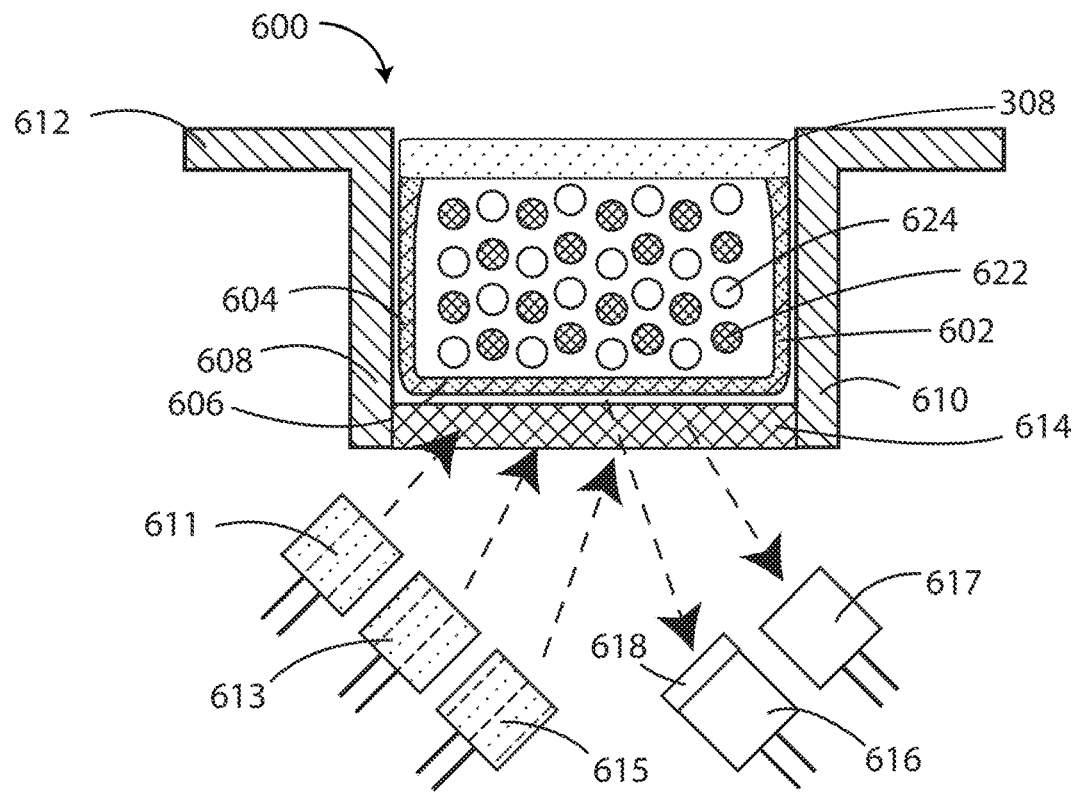
FIG. 6 is a schematic cross-sectional view of an analyte sensor in accordance with various embodiments herein.
Figure 7:
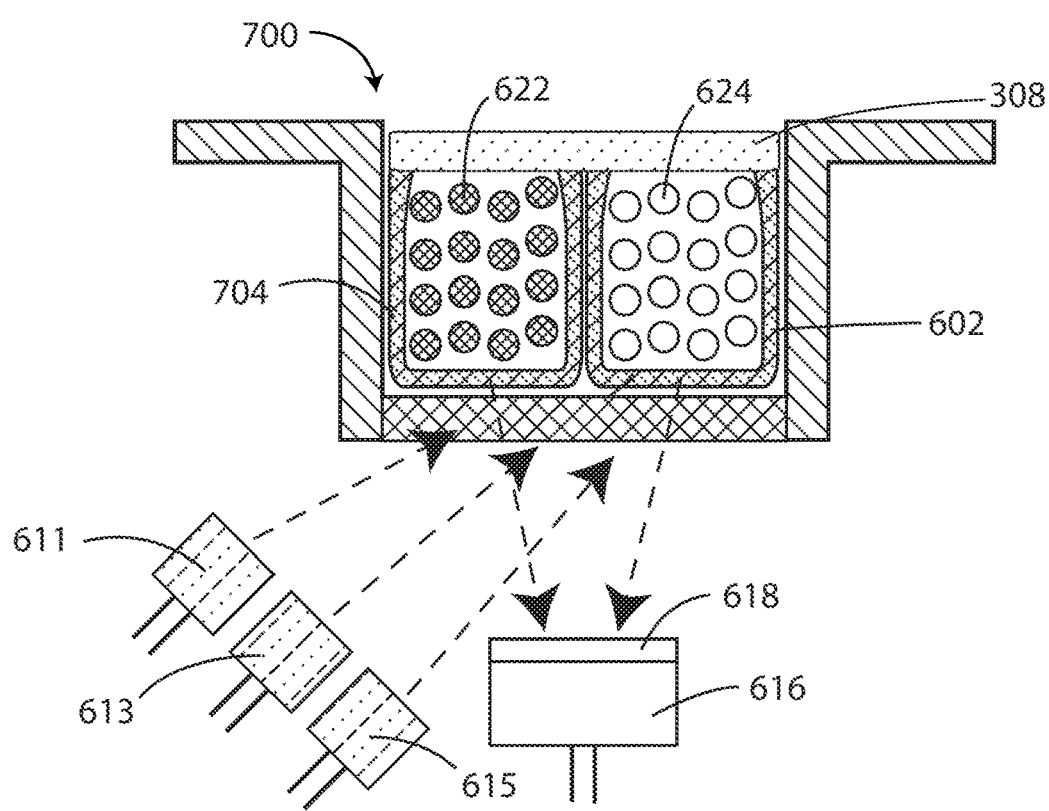
FIG. 7 is a schematic cross-sectional view of an analyte sensor in accordance with various embodiments herein.

While FIG. 3 shows light rays reflecting and/or absorbing near the bottom of the sensing elements, it will be appreciated that this is merely for ease of illustration and that the entire sensing element can be exposed to light from the optical excitation assemblies and therefore contribute to generating a response that can be detected by the optical detection assemblies (with similar comments applying to FIGS. 4, 6 and 7).

In accordance with the embodiments herein, some of the analyte sensors can also include a bioerodible masking layer disposed on or over the exterior surface of the analyte sensor or the analyte window (if one is included) so as to shield the analyte sensors from the implant environment until a predetermined point in time. Masking layer can be formed from various bioerodible polymers including, but not limited to, polylactic acid, poly-L-lactic acid, and derivatives thereof. Additional masking layer materials and their physical properties suitable for use with the embodiments herein are described more fully below.

Referring now to FIG. 4, a schematic cross-sectional view of an IMD in accordance with various embodiments herein is shown. The IMD can include implantable housing 102. The implantable housing 102 of can include various materials such as metals, polymers, ceramics, and the like. In some embodiments, the implantable housing 102 can be a single integrated unit. In other embodiments, the implantable housing 102 can include implantable housing 102 and header 104 (not shown), as discussed above. In some embodiments, the implantable housing 102, or one or more portions thereof, can be formed of titanium. In some embodiments, one or more segments of the implantable housing 102 can be hermetically sealed.

Implantable housing 102 can define an interior volume 404 that in some embodiments is hermetically sealed off from the area 406 outside of the IMD. The IMD can include circuitry 408, which can be disposed within the interior volume 404, within the header (see 104 in FIG. 1), or distributed between both. Circuitry 408 can include various components, such as components 410, 412, 414, 416, 418, and 420. In some embodiments, these components can be integrated and in other embodiments these components can be separate. In some embodiments, the components can include one or more of a microprocessor, memory circuitry (such as random-access memory (RAM) and/or read-only memory (ROM)), recorder circuitry, telemetry circuitry, analyte sensor interface circuitry, power supply circuitry (which can include one or more batteries), normalization circuitry, analyte sensor control circuitry, and the like. In some embodiments recorder circuitry can record the data produced by the analyte sensor and record time stamps regarding the same. In some embodiments, the circuitry can be hardwired to execute various functions, while in other embodiments the circuitry can be implemented as instructions executing on a microprocessor or other computation device.

The circuitry 408 can include a control circuit and can be configured to receive (directly or indirectly) a signal from the optical detection assembly or cause another component to receive a signal from the optical detection assembly.

In some embodiments, the circuitry 408 can be configured to calculate a concentration of two or more analytes using signals received from the optical detection assembly. In the context of a colorimetric mode, this can be done by comparing the amplitude of signals at two or more frequencies and then calculating a concentration of the analyte based on the comparison. Many different specific techniques can be used for calculating a concentration based on a colorimetric signal or signals. In the context of a photoluminescent mode, this can be done by measuring the amplitude of a signal(s) at a characteristic response frequency wherein the amplitude correlates to a concentration of a particular analyte. However, in other cases, concentration of the analyte can be determined by calculating a response-time constant and then determining a concentration based on a correlation to the calculated response-time constant. Many different specific techniques can be used for calculating a concentration based on a photoluminescent signal or signals.

It will be appreciated that signal(s) herein can be subject to various intermediate steps including, but not limited to, filtering, amplification, analog to digital conversion, digital to analog conversion, and the like.

A telemetry interface 422 can be provided for communicating with external devices such as a programmer, a home-based unit, and/or a mobile unit (e.g., a cellular phone, portable computer, etc.). In some embodiments telemetry interface 422 can be provided for communicating with implanted devices such as a therapy delivery device (e.g. a pacemaker or cardioverter-defibrillator) or a monitoring-only device (e.g. an implantable loop recorder). In some embodiments, the circuitry can be implemented remotely, via either near-field, far-field, conducted, intra-body, or extracorporeal communication, from instructions executing on any of the external or the implanted devices, etc. In some embodiments, the telemetry interface 422 can be located within implantable housing 102. In some embodiments, the telemetry interface 422 can be located in header 104.

The optical excitation 312, 313 and optical detection 314 assemblies of the analyte sensors embodied herein can be in electrical communication with the circuitry 408 within the interior volume 404. In some embodiments, the control circuitry 408 can be configured to selectively activate the optical excitation 312, 313 and optical detection 314 assemblies of the analyte sensors embodied herein.

Figure 5:
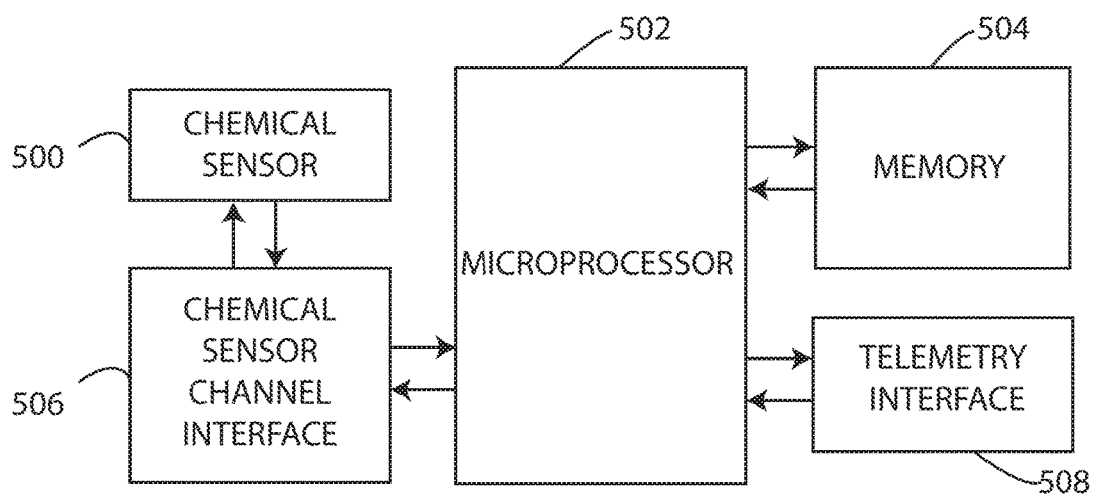
FIG. 5 is a schematic diagram of components of an implantable medical device in accordance with various embodiments herein.

Referring now to FIG. 5, a schematic diagram of components of the implantable medical devices in accordance with various embodiments herein. It will be appreciated that some embodiments can include additional elements beyond those shown in FIG. 5. In addition, some embodiments may lack some elements shown in FIG. 5. The IMD can gather information through one or more sensing channels. A microprocessor 502 can communicate with a memory 504 via a bidirectional data bus. The memory 504 can include read-only memory (ROM) or random-access memory (RAM) for program storage and RAM for data storage, or any combination thereof. The implantable medical device can also include one or more analyte sensors 500 and one or more analyte sensor channel interfaces 506 which can communicate with a port of microprocessor 502. The analyte sensor channel interface 506 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like. A telemetry interface 508 is also provided for communicating with external devices such as a programmer, a home-based unit, and/or a mobile unit (e.g., a cellular phone, portable computer, etc.), implanted devices such as a pacemaker, cardioverter-defibrillator, loop recorder, and the like.

Referring now to FIG. 6, a cross-sectional view of an analyte sensor 600 in accordance with the embodiments herein is shown. Analyte sensor 600 can include sensing element 602 and analyte window 308, which can be part of the sensing element 602. The sensing element 602 can include an outer barrier layer 604 formed, in full or in part, from a permeable material, such as the ion permeable polymeric matrix materials as described below. In some embodiments, at least a portion of the outer barrier layer 604 is formed of polyHEMA, agarose, alginates, polyvinyl alcohol, polyacrylate, collagen, PEG, gelatin, glass, borosilicate glass, or mixtures or derivatives thereof. Outer barrier layer 604 can include a bottom 606, and opposed sides 608 and 610 to surround an interior volume of sensing element 602. In some embodiments, analyte window 308 can be integrated with and/or form the top of the outer barrier layer 604 and in some cases be the same material as the other portions of the outer barrier layer 604. In other embodiments, analyte window 308 can be formed from a different material than the outer barrier layer 604. In some embodiments, only the analyte window 308 can be permeable to an analyte. In some embodiments, the entire outer barrier layer 604 can be permeable to an analyte. In some embodiments, the analyte window can be created from the ion permeable polymeric matrix material, polyhydroxyethyl methacrylate (polyHEMA).

In some embodiments, the implantable housing 102 (see FIG. 1) can include a recessed pan 612 into which the sensing element 602 fits. In some embodiments, the top of the recessed pan 612 can be substantially flush with the top of the sensing element 602. In other embodiments, the top of the recessed pan 612 can be higher than the top of the sensing element 602 so as to create a space between the top of the sensing element 602 and the top of the recessed pan 612. In some embodiments, the sensing element 602 may lack an outer barrier layer and the surfaces of the recessed pan 612 can be used to hold the sensor element components.

In some embodiments, the implantable housing 102 (see FIG. 1) can define an aperture occluded by a transparent member 614. The transparent member 614 can be a glass (including but not limited to borosilicate glasses), a polymer or other transparent material. The aperture can be disposed at the bottom of the recessed pan 612. The aperture can provide an interface allowing for optical communication between sensing element 602 and the optical excitation 611, 613, 615 and optical detection 616, 617 assemblies.

It will be appreciated that outer barrier layer 604, or portions thereof such as the bottom 606, can be made from a transparent polymer matrix material to allow for optical communication between the sensing element 602 and optical excitation 611, 613, 615 and optical detection 616, 617 assemblies. In will be appreciated, however, that bottom 606 of sensing element 602 may or may not be a discrete material or layer. For example, in some embodiments, bottom 606 and the transparent member 614 may be layers of different materials or may be the same type of material.

The optical excitation assemblies 611, 613, 615 can be configured to illuminate the sensing element 602. Optical excitation assemblies 611, 613, 615 can include a light source such as a light emitting diode (LED), vertical-cavity surface-emitting lasers (VCSELs), electroluminescent (EL) devices, and the like. Optical excitation assemblies herein can include broadband emitters and narrowband emitters. In some embodiments, optical excitation assemblies herein can emit electromagnetic waves primarily at a particular frequency or frequency band (primary frequency). Some optical excitation assemblies herein can produce light within the visible spectrum (e.g., 395 nm to 700 nm) and some can produce light within the ultraviolet (UV) spectrum (e.g., 10 nm to 395 nm), or near-infrared (NIR) spectrum (e.g., 700 nm to 1.5 or 2.0 µm). Some optical excitation assemblies herein can produce electromagnetic waves at frequencies outside of the preceding frequency ranges. In some embodiments, each optical excitation assembly can include a single emitter. In other embodiments, each optical excitation assembly can include more than one emitter, such as 2, 3, 4, 5, 6, 7, 8 or more emitters. In some particular embodiments, each analyte (or chemical) sensor herein can include one or two emitters operating within the visible spectrum and at least one emitter selected from those operating with the UV spectrum and those operating within the near-infrared (NIR) spectrum.

The optical detection assemblies 616, 617 can receive light and generate a signal. In some embodiments an optical filter 618, such as a low pass optical filter or a band pass optical filter can be disposed over at least one of the optical detection assemblies. The optical detection assemblies 616, 617 can be in communication with other circuitry of the device in order to deliver the signal for further processing. Optical detection assemblies 616, 617 can include a component selected from the group consisting of a photodiode, a phototransistor, a charge-coupled device (CCD), a junction field effect transistor (JFET) optical sensor, a complementary metal-oxide semiconductor (CMOS) optical sensor, an integrated photo detector integrated circuit, a light to voltage converter, and the like. Optical excitation 611, 613, 615 and optical detection 616, 617 assemblies are discussed in further detail below. Briefly, however, the optical excitation assemblies can be configured to emit light at one or more visible spectrum frequencies, at one or more ultraviolet frequencies, or one or more near-infrared (NIR) frequencies. While two optical excitation assemblies are shown in combination with a single optical detection assembly, it will be appreciated that the numbers of excitation assemblies and detection assemblies are not so limited. Indeed, various numbers of excitation assemblies and detection assemblies are specifically contemplated herein.

The sensing element 602 can be multimodal. By way of example, the sensing element 602 can be both colorimetric and photoluminescent. For example, the sensing element 602 can include a colorimetric response element specific for a first chemical analyte and a photoluminescent response element specific for a second chemical analyte. In some cases, the photoluminescent response element is fluorescent. In some cases, the photoluminescent response element is phosphorescent. As such, the sensing element can include response elements of a first type 622 and response elements of a second type 624. In some cases, response elements of the first type 622 can be colorimetric while the response elements of the second type 624 can be photoluminescent. In some cases, response elements of the first type 622 can be photoluminescent while the response elements of the second type 624 can be colorimetric. In some embodiments, both the response elements of the first type 622 and the response elements of the second type 624 can be fluorescent, but they can operate in a non-overlapping manner, such that one is triggered by wavelength A and one is triggered by wavelength B, and wavelengths A and B are not the same.

In the example illustrated by FIG. 6, the response elements (such as the colorimetric response elements and the photoluminescent response elements) are both disposed throughout (such as evenly dispersed throughout) the interior volume of the sensing element 602. However, in some embodiments, the response elements may be only disposed in certain portions of the interior volume of the sensing element 602. In some embodiments, response elements of the first type 622 and response elements of the second type 624 can be segregated from one another into different portions of the interior volume of the sensing element 602.

The response elements (first type 622 and second type 624) in FIG. 6 are shown in the form of beads. The beads can include a polymer matrix (e.g., polymeric beads), porous glass material, or another type of porous or non-porous material. Various chemistries described below can be disposed within and/or bonded to the polymer matrix of porous glass material. The beads can have various diameters which can be all the same or can be different, such as different between different response element types). However, it will be appreciated that beads are merely one physical form that the response elements can take. Indeed, many different shapes and forms of response elements are contemplated herein.

In some embodiments, multiple sensing elements can be used. In some cases, response elements of different types can be segregated into different sensing elements. Referring now to FIG. 7, a schematic cross-sectional view of an analyte sensor 700 in accordance with various embodiments herein. The analyte sensor 700 can include first sensing element 602, second sensing element 704, and shared analyte window 308. However, in other embodiments, each sensing element can have its own discrete analyte window.

Each sensing element 602, 704 can include an outer barrier layer formed, in full or in part, from a permeable material, such as the ion permeable polymeric matrix materials as described below. The outer barrier layer can include a bottom, and opposed sides surrounding an interior volume of sensing elements 602, 704. In some embodiments, analyte window 308 can be integrated with and/or form the top of the outer barrier layer of one or both sensing elements. In other embodiments, the analyte window can be a separate structure.

The optical excitation assemblies 611, 613, 615 can be configured to illuminate the sensing elements 602, 704. Optical detection assembly 314 can be configured to detect light reflected from or emitted by the sensing element 602, 704.

The sensing element 602, 704 can be multimodal. The sensing element 602, 704 can include response elements of a first type 622 and response elements of a second type 624. Response elements of the first type 622 can be colorimetric while the response elements of the second type 624 can be photoluminescent. In some cases, response elements of the first type 622 can be photoluminescent while the response elements of the second type 624 can be colorimetric.

Figure 8:
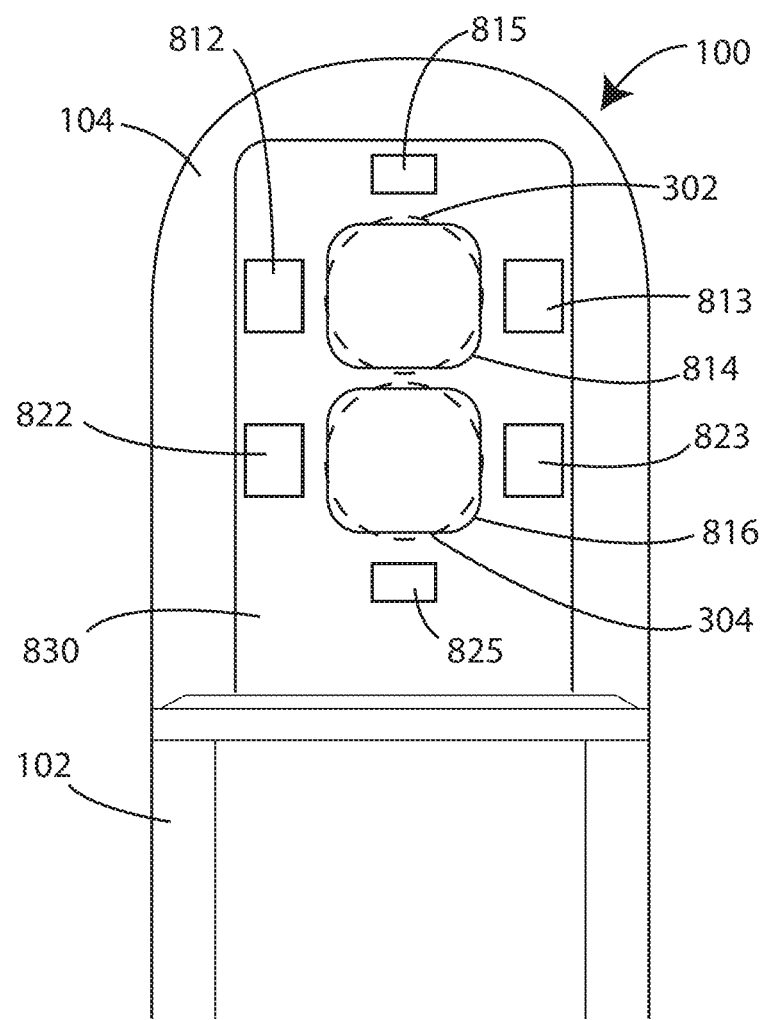
FIG. 8 is a schematic partial cut-away view of a portion of an implantable medical device in accordance with various embodiments herein.

Referring now to FIG. 8, a schematic partial cut-away view of a portion of an implantable medical device 100 in accordance with various embodiments herein. In this view, a circuit board 830 (or other type of supporting structure or substrate) is shown with optical excitation assemblies and optical detection assemblies mounted thereon. In particular, optical excitation assemblies 812, 813, 815, 822, 823, and 825 are shown disposed on the circuit board 830. In some embodiments, optical excitation assemblies to the sides (e.g., 812, 813, 822, and 823) relative to optical detection assemblies 814, 816 include visible spectrum emitters while optical excitation assemblies in the front and back (815 and 825) relative to optical detection assemblies 814, 816 can include UV or NIR emitters. The position of sensing elements 302, 304 is shown in broken lines over the optical detection assemblies 814, 816. However, it will be appreciated that the sensing elements 302, 304 can also be located in different positions. In some embodiments, optical excitation assemblies on one side (such as 812 and 822) include emitters that primarily emit light in the red frequency spectrum of visible light while optical excitation assemblies on the other side (such as 813 and 823) include emitters that primarily emit light in the green frequency spectrum of visible light.

Figure 9:
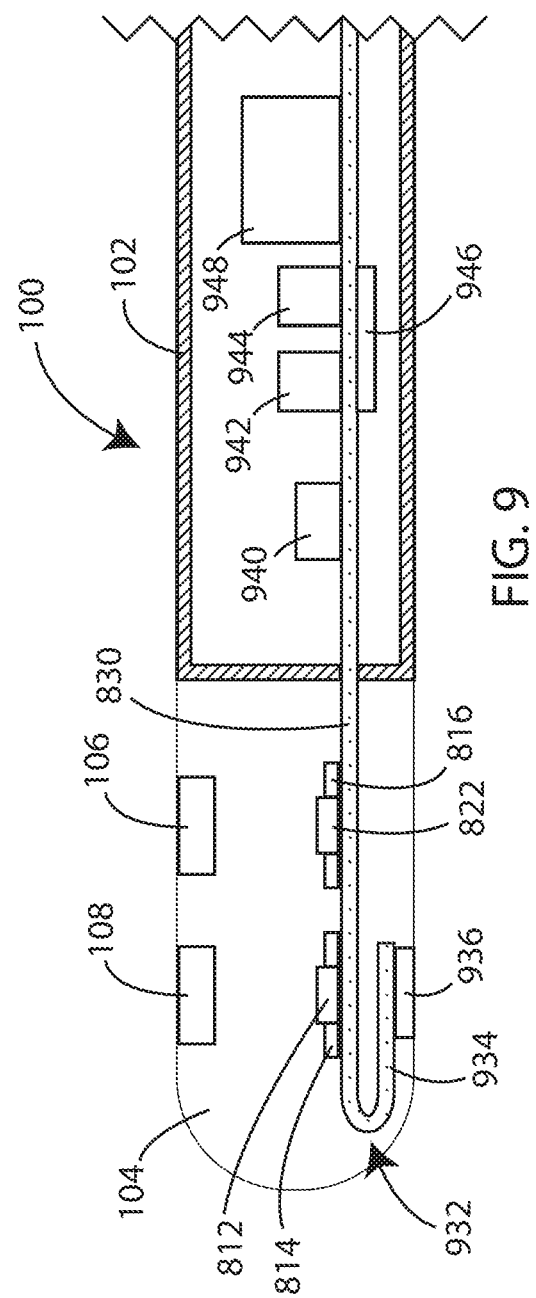
FIG. 9 is a schematic cross-sectional view of a portion of an implantable medical device in accordance with various embodiments herein.

Referring now to FIG. 9, a schematic cross-sectional view of a portion of an implantable medical device 100 is shown in accordance with various embodiments herein. In this example, the circuit board 830 (or other support structure) includes a curved portion 932 that causes the circuit board 830 to overlap itself. In particular, the circuit board 803 includes a hairpin turn and has a segment 934 overlapping other portions of the circuit board 830. In some embodiments, the curved portion 932 can change the direction of the circuit board 830 by about 90, 100, 110, 120, 130, 140, 150, 160, 170 or 180 degrees, or by an amount falling within a range wherein any of the preceding can serve as the upper or lower bound of the range. The circuit board 830 (or other support structure) can extend between the implantable housing 102 and the header 104. Various electronic components 940, 942, 944, 946, and 948 can be mounted on the circuit board 830 within the implantable housing 102. It will be appreciated, however, that in some embodiments there is not a distinct housing and header, rather there can be a single structure functioning as both a housing and a header.

In some embodiments, other components can be mounted on the overlapping segment 934. By way of example, in some embodiments, a surface component (e.g., a component that is mounted on or within the surface of the implantable housing 102 or header 104) can be mounted on the overlapping segment 934. As a specific example, an electrode 936 can be mounted on the overlapping segment 934 and can be in contact with the surface of the header 104 such that the electrode 936 contacts tissues of the body when the device is implanted.

In some embodiments, one or more portions of the circuit board 830 (or similar support structure) can be angled in order to allow for components to be flush-mounted onto the circuit board 830 and yet be pointed in a desirable direction with respect to other components of the system.

Figure 10:
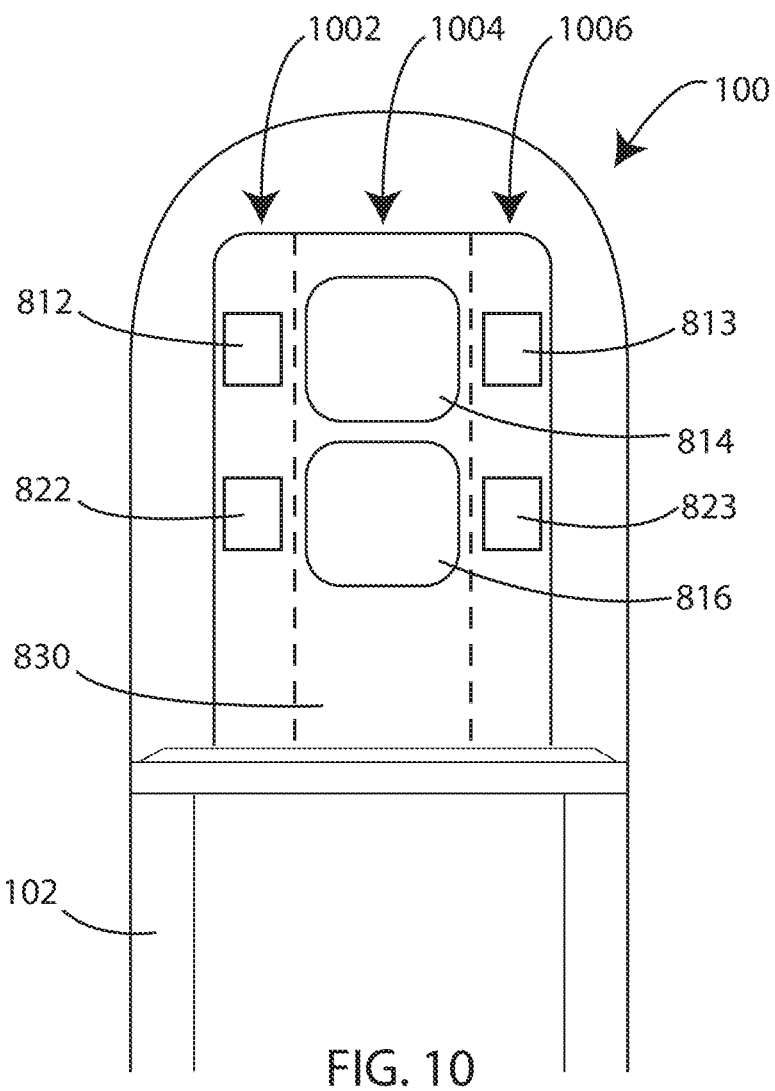
FIG. 10 is a schematic partial cut-away view of a portion of an implantable medical device in accordance with various embodiments herein.

Referring now to FIG. 10, a schematic partial cut-away view is shown of a portion of an implantable medical device 100 in accordance with various embodiments herein. In this view, the circuit board 830 includes a first portion 1002 (or first side wing), a second portion 1004 and a third portion 1006 (or second side wing). The first portion 1002 and the third portion 1006 can be angled upward with respect to the second portion 1004 which can be disposed in the middle between the first portion 1002 and the third portion 1006. As such, optical excitation assemblies 812, 822, which are mounted on the first portion 1002 can be pointed slightly inward toward the second portion 1004. Further, optical excitation assemblies 813, 823, which are mounted on the third portion 1006 can be pointed slightly inward toward the second portion 1004.

Figure 11:
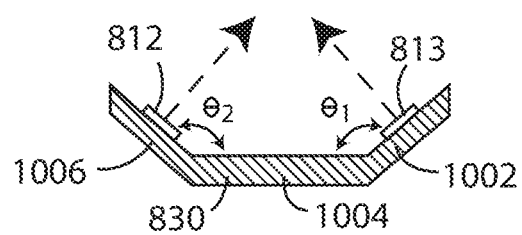
FIG. 11 is a schematic cross-sectional elevation view of a portion of an implantable medical device in accordance with various embodiments herein.

The arrangement of FIG. 10 can be clearly observed in FIG. 11. FIG. 11 is a schematic cross-sectional elevation view of a portion of an implantable medical device 100 in accordance with various embodiments herein. In this view, it can be seen that the first portion 1002 is angled upward with respect to second portion 1004 by an angle represented by theta sub 1. Theta sub 1 can be about 5, 10, 15, 20, 25, 30, 40, 50, 60, 70, 80 or 90 degrees, or it can fall within a range wherein any of the foregoing angles can serve as the upper or lower bound of the range. Similarly, third portion 1006 is angled upward with respect to second portion 1004 by an angle represented by theta sub 2. Theta sub 2 can be about 5, 10, 15, 20, 25, 30, 40, 50, 60, 70, 80 or 90 degrees, or it can fall within a range wherein any of the foregoing angles can serve as the upper or lower bound of the range. As such, optical excitation assemblies disposed on either the first portion 1002 or the third portion 1006 can be pointed inward at an angle with respect to vertical (or with respect to an axis that is perpendicular to the middle portion or second portion of the circuit board) by an angle of about 5, 10, 15, 20, 25, 30, 40, 50, 60, 70, 80 or 90 degrees, or it can fall within a range wherein any of the foregoing angles can serve as the upper or lower bound of the range. In some embodiments, all of the optical excitation assemblies can be pointed inward in this manner. In other embodiments, only a subset of the total number of optical excitation assemblies are pointed inward in this manner. In some embodiments, it will be appreciated that an angled riser or similar structure can be used to cause the optical excitation assemblies to be pointed inward.

In some embodiments, a body member or similar structure can be used as a structure to which other components are attached. Such a body member or similar structure can facilitate proper placement of components as well as facilitate mounting of the components either within a header or a housing (such as within an aperture in the header or housing).

Referring now to FIG. 12, a schematic cross-sectional view is shown of a portion of an implantable medical device in accordance with various embodiments herein.

A body member 1202 can be included and can interface with portions of a wall member 1270 can may be part of an exterior wall of the housing 102 or header 104. In some embodiments, the body member 1202 can have pre-formed cavities to accommodate light fiber or air pockets for a desired light path between the optical excitation assemblies 312, 313, 1212, 1213 and the sensing elements 302, 304 and/or between the sensing elements 302, 304 and the optical detection 314, 1214 assemblies. The body member 1202 can include pans (or depressions or cavities) into which sensing element 302 and sensing element 304 can be disposed. In some embodiments, an analyte window 308 can be disposed over the sensing elements. In some embodiments, the analyte window can be an integrated portion of the sensing elements. In some embodiments, a guard or membrane 1230 can be disposed over the analyte window 308. In some embodiments, the guard or membrane 1230 can be opaque to the passage of light in the visible, UV and/or NIR frequency spectrums.

The optical excitation assemblies 312, 313, 1212, and 1213, and optical detection assemblies 314, 1214 can be mounted on a surface of the body member 1202. For example, such components can be mounted on a bottom surface of the body member 1202 (a surface that is opposite the surface wherein the pans or depressions are disposed). In some embodiments, portions of the bottom surface of the body member 1202 can be angled with respect to the sensing elements in order to result in better directional alignment with the sensing element 302 and sensing element 304. In some embodiments, optical excitation assemblies 312 and 313 can be mounted on discrete portions of the bottom surface of the body member 1202 that are angled toward the sensing element 302, while the optical detection assembly 314 can be mounted on a substantially flat non-angled portion, which in some cases can be direction below the sensing element 302. Similarly, in some embodiments, the optical excitation assemblies 1212, 1213 can be mounted on discrete portions of the bottom surface of the body member 1202 that are angled toward the sensing element 304, while the optical detection assembly 1214 can be mounted on a substantially flat non-angled portion.

The body member 1202 can be formed from various materials. In some embodiments, the body member 1202 can be formed of a transparent polymer, glass, or the like. In some embodiments, the body member 1202 can be pre-formed and then other components can be mounted thereon. In other embodiments, the body member 1202 can be formed in-situ by holding components in place and then using a flowable composition (such as a polymeric composition and/or adhesive composition) that can then be cooled or cured to form a solid material.

Referring now to FIG. 13, a schematic cross-sectional view is shown of a portion of an implantable medical device in accordance with various embodiments herein. In this embodiment, the body member 1202 again includes pans or depressions into which the sensing elements 302, 304 can fit. The body member 1202 also has optical excitation assemblies 312, 313, 1212, and 1213 mounted thereon along with optical detection assemblies 314, 1214. Optical excitation assemblies and adjoining optical detection assemblies can be separated by shrouds 1240 in order to prevent direct light leakage from excitation assemblies to the detection assemblies. In some embodiments, a dividing shroud 1242 can be used to optically isolate components functioning with the first sensing element 302 from components function with the second sensing element 304. In this embodiment, the optical excitation assemblies 312, 313, 1212, and 1213 can all be mounted such that directionally they are facing straight upward instead of angled toward the sensing elements. In this matter, the optical excitation assemblies can be mounted in a plane that is substantially parallel to the plane in which the optical detection assemblies are mounted. The body member 1202 can be pre-formed or formed in-situ by holding components in place and then using a flowable composition (such as a polymeric composition and/or adhesive composition) that can then be cooled or cured to form a solid material.

Analyte Sensors

Analyte sensors herein can be of various types. In some embodiments, the physiological concentration of an analyte is sensed directly. In other embodiments, the physiological concentration of an analyte is sensed indirectly. By way of example, a metabolite of a particular analyte can be sensed instead of the particular analyte itself. In other embodiments, an analyte can be chemically converted into another form in order to make the process of detection easier. By way of example, an enzyme can be used to convert an analyte into another compound that is easier to detect. For example, the hydrolysis of creatinine into ammonia and N-methylhydantoin can be catalyzed by creatinine deiminase and the resulting ammonia can be detected by an analyte sensor. In some embodiments, analyte sensors herein can include at least two functional elements: a receptor and a transducer. It will be appreciated that other elements can also be included. The receptor part of an analyte sensor can transform analyte information into a form of energy or signal that can be measured by the transducer. The transducer can transform and/or convey the energy or signal carrying the analyte information so as to provide a useful analytical signal.

Analyte sensors can include optical devices that utilize changes of optical phenomena or properties, which are the result of an interaction of the analyte with the receptor part of the sensor. Such optical properties can include: absorbance, caused by the absorptivity of the analyte itself or by a reaction with some suitable indicator; reflectance, using a bodily component, tissue, or fluid, or using an immobilized indicator; photoluminescence, based on the measurement of the intensity of light emitted by a chemical reaction in the receptor system; fluorescence, measured as the positive emission effect caused by irradiation or selective quenching of fluorescence; refractive index, measured as the result of a change in solution composition, in some cases including surface plasmon resonance effects; optothermal effects, based on a measurement of the thermal effect caused by light absorption; light scattering; or the like. In some embodiments, optical analyte sensors can include an optode.

Analyte sensors can also include electrochemical devices that transform the effect of the electrochemical interaction between an analyte and an electrode into a useful signal. Such sensors can include voltammetric sensors, including amperometric devices. Also included are sensors based on chemically inert electrodes, chemically active electrodes and modified electrodes. Also included are sensors with and without (galvanic sensors) a current source. Sensors can also include potentiometric sensors, in which the potential of the indicator electrode (ion-selective electrode, redox electrode, metal oxide electrode, or the like) is measured against a reference electrode. Sensors can include chemically sensitized field effect transistors (CHEMFET) in which the effect of the interaction between the analyte and the active coating is transformed into a change of the source-drain current. Sensors can include potentiometric solid electrolyte gas sensors.

Analyte sensors can also include electrical devices based on measurements, where no electrochemical processes take place, but the signal arises from the change of electrical properties caused by interaction with the analyte. Such sensors can include metal oxide semiconductor sensors based on reversible redox processes of analyte gas components, organic semiconductor sensors, based on the formation of charge transfer complexes, which modify the charge carrier density, electrolytic conductivity sensors, and electric permittivity sensors.

Analyte sensors can also include mass sensitive devices that transform the mass change at a specially modified surface into a change of a property of the support material. The mass change can be caused by accumulation of the analyte. Such sensors can include piezoelectric devices based on the measurement the frequency change of the quartz oscillator plate caused by adsorption of a mass of the analyte at the oscillator and surface acoustic wave devices that depend on the modification of the propagation velocity of a generated acoustical wave affected by the deposition of a definite mass of the analyte.

Analyte sensors can also include magnetic devices based on the change of paramagnetic properties of a gas being analyzed. Analyte sensors can also include thermometric devices based on the measurement of the heat effects of a specific chemical reaction or adsorption that involves the analyte.

In one example of the operation of an optical analyte sensor, analytes of interest from the in vivo environment can diffuse into an analyte sensing element causing a detectable change in the optical properties of the analyte sensing element. Light can be generated by an optical excitation device or emitter, such as an LED or similar device, and can pass through the optical window and into the analyte sensing element. Light can then either be preferentially reflected from or re-emitted by the analyte sensing element proportionally to the sensed analyte and pass back through the optical window before being received by a light detection device or receiver, such as a charge-coupled device (CCD), a photodiode, a junction field effect transistor (JFET) type optical sensor, of complementary metal-oxide semiconductor (CMOS) type optical sensor. Various aspects of exemplary analyte sensors are described in greater detail in U.S. Pat. No. 7,809,441, the content of which is herein incorporated by reference in its entirety. In another example of the operation of an optical analyte sensor, the optical properties of a tissue or fluid in the body can be directly analyzed. By way of example, light can be generated by an optical excitation device that can be delivered to a component, tissue, or fluid in the body and a light detection device can be used to sense an optical property of the light that has interfaced with the component, tissue, or fluid.

In accordance with the embodiments herein, some sensing element(s) can include one or more ion-selective sensors. Ion-selective sensors may either rely on surface phenomena or on concentration changes inside the bulk of a phase. Ion-selective sensors can include optical sensors, including both non-carrier optical sensors and carrier-based optical sensors, and ion-selective electrodes (ISEs). In some embodiments, the ion-selective sensor is fluorimetric, and can include a complexing moiety and a fluorescing moiety. Fluorimetric ion-selective sensors can exhibit differential fluorescent intensity based upon the complexing of an analyte to a complexing moiety. In some embodiments, the ion-selective sensor can be colorimetric, and can include a complexing moiety and a colorimetric moiety. Colorimetric ion-selective sensors can exhibit differential light absorbance based upon the complexing of an analyte to a complexing moiety.

In some embodiments, the ion-selective sensor comprises a non-carrier or carrier-based fluorescent or colorimetric ionophoric composition that comprises a complexing moiety for reversibly binding an ion to be analyzed, and a fluorescing or colorimetric moiety that changes its optical properties as the complexing agent binds or releases the ion. The complexing agents of the invention can optionally be appended with one or more organic substituents chosen to confer desired properties useful in formulating the ion sensing composition. By way of example, the substituents can be selected to stabilize the complexing agent with respect to leaching into the solution to be sensed, for example, by incorporating a hydrophobic or polymeric tail or by providing a means for covalent attachment of the complexing agent to a polymer support within the ion-selective sensor.

In some embodiments, the sensing element can include ion-selective sensors such as an ionophore or a fluorionophore. Suitable ionophores for use with the embodiments herein can include, but not be limited to, sodium specific ionophores, potassium specific ionophores, calcium specific ionophores, magnesium specific ionophores, and lithium specific ionophores. Suitable fluorionophores for use with the embodiments herein can include, but not be limited to, lithium specific fluoroionophores, sodium specific fluoroionophores, and potassium specific fluoroionophores.

Exemplary ion-selective sensors and methods for their use are disclosed in commonly assigned U.S. Pat. No. 7,809,441, the contents of which is herein incorporated by reference in its entirety.

Colorimetric and Photoluminescent Chemistries

Colorimetric response elements herein can be specific for a particular chemical analyte. Colorimetric response elements can include an element that changes color based on binding with or otherwise complexing with a specific chemical analyte. In some embodiments, a colorimetric response element can include a complexing moiety and a colorimetric moiety. Those moieties can be a part of a single chemical compound (as an example a non-carrier based system) or they can be separated on two or more different chemical compounds (as an example a carrier based system). The colorimetric moiety can exhibit differential light absorbance on binding of the complexing moiety to an analyte.

Photoluminescent response elements herein can be specific for a particular chemical analyte. Photoluminescent response elements herein can include an element that absorbs and emits light through a photoluminescent process, wherein the intensity and/or wavelength of the emission is impacted based on binding with or otherwise complexing with a specific chemical analyte. In some embodiments, a photoluminescent response element can include a complexing moiety and a fluorescing moiety. Those moieties can be a part of a single chemical compound (as an example a non-carrier based system) or they can be separated on two or more different chemical compounds (as an example a carrier based system). In some embodiments, the fluorescing moiety can exhibit different fluorescent intensity and/or emission wavelength based upon binding of the complexing moiety to an analyte.

Some chemistries may not require a separate compound to both complex an analyte of interest and produce an optical response. By way of example, in some embodiments, the response element can include a non-carrier optical moiety or material wherein selective complexation with the analyte of interest directly produces either a colorimetric or fluorescent response. As an example, a fluoroionophore can be used and is a compound including both a fluorescent moiety and an ion complexing moiety. As merely one example, (6,7-[2.2.2]-cryptando-3-[2"-(5"-carboethoxy)thiophenyl]coumarin, a potassium ion selective fluoroionophore, can be used (and in some cases covalently attached to polymeric matrix or membrane) to produce a fluorescence-based $K^+$ non-carrier response element.

An exemplary class of fluoroionophores are the coumarocryptands. Coumarocryptands can include lithium specific fluoroionophores, sodium specific fluoroionophores, and potassium specific fluoroionophores. For example, lithium specific fluoroionophores can include (6,7-[2.1.1]-cryptando-3-[2"-(5"-carboethoxy)furyl]coumarin. Sodium specific fluoroionophores can include (6,7-[2.2.1]-cryptando-3-[2"-(5"-carboethoxy)furyl]coumarin. Potassium specific fluoroionophores can include (6,7-[2.2.2]-cryptando-3-[2"-(5"-carboethoxy)furyl]coumarin and (6,7-[2.2.2]-cryptando-3-[2"-(5"-carboethoxy)thiophenyl]coumarin.

Suitable fluoroionophores include the coumarocryptands taught in U.S. Pat. No. 5,958,782, the disclosure of which is herein incorporated by reference. Such fluorescent ionophoric compounds can be excited with GaN blue light emitting diodes (LEDs) emitting light at or about 400 nm. These fluorescent ionophoric compounds have ion concentration dependent emission that can be detected in the wavelength range of about 450 nm to about 470 nm.

Some chemistries can rely upon a separate complexing entity (e.g., a separate chemical compound). As an example, carrier based response elements can include a compound, in some cases referred to as an ionophore, that complexes with and serves to carry the analyte of interest. In some embodiments, carrier based response elements include a lipophilic ionophore, and a lipophilic fluorescent or colorimetric indicator dye, called a chromoionophore. In some cases the chromoionophore and the ionophore can be dispersed in, and/or covalently attached to, a hydrophobic organic polymeric matrix. The ionophore can be capable of reversibly binding ions of interest. The chromoionophore can be a proton selective dye. In operation, analytes of interest are reversibly sequestered by the ionophores within the organic polymer matrix. To maintain charge neutrality within the polymer matrix, protons are then released from the chromoionophore, giving rise to a color or fluorescence change. As just one specific example, a carrier based response element can include potassium ionophore III, chromoionophore I, and potassium tetrakis(4-chlorophenyl)borate dispersed in a polymer matrix made from polyvinylchloride and bis(2-ethylhexyl)sebacate surfactant to produce a colorimetric sensing element.

Both non-carrier based response elements and carrier-based response elements can include complexing moieties. Suitable complexing moieties can include cryptands, crown ethers, bis-crown ethers, calixarenes, noncyclic amides, and hemispherand moieties as well as ion selective antibiotics such as monensin, valinomycin and nigericin derivatives.

Those of skill in the art can recognize which cryptand and crown ether moieties are useful in complexing particular cations, although reference can be made to, for example, Lehn and Sauvage, "[2]-Cryptates: Stability and Selectivity of Alkali and Alkaline-Earth Macrocyclic Complexes," J. Am. Chem. Soc, 97, 6700-07 (1975), for further information on this topic. Those skilled in the art can recognize which bis-crown ether, calixarene, noncyclic amides, hemispherand, and antibiotic moieties are useful in complexing particular cations, although reference can be made to, for example, Buhlmann et al., "Carrier-Based Ion-Selective Electrodes and Bulk Optodes. 2. Ionophores for Potentiometric and Optical Sensors," Chem. Rev. 98, 1593-1687 (1998), for further information on this topic.

By way of example cryptands can include a structure referred to as a cryptand cage. For cryptand cages, the size of the cage is defined by the oxygen and nitrogen atoms and the size makes cryptand cages quite selective for cations with a similar diameter. For example a [2.2.2] cryptand cage is quite selective for cations such as $K^+$, $Pb^{+2}$, $Sr^{+2}$, and $Ba^{+2}$. A [2.2.1] cryptand cage is quite selective for cations such as $Na^+$ and $Ca^{+2}$. Finally, a [2.1.1] cryptand cage is quite selective for cations such as $Li^+$ and $Mg^{+2}$. The size selectivity of cryptand cages can aid in the sensitivity of chemical sensing. When these cryptand cages are incorporated into physiologic sensing systems heavier metals such as $Pb^{+2}$ and $Ba^{+2}$ are unlikely to be present in concentrations which interfere with the analysis of ions of broader physiological interest such as $Na^+$ and $K^+$.

In some embodiments, sensing elements can operate using multiple non-overlapping fluorescence modes. For example, two or more fluorescent indicators can be used with one triggered by a first wavelength "A" of light and one triggered by a different wavelength "B" of light. Many combinations of colorimetric and photoluminescent sensing elements are contemplated herein.

Further aspects of colorimetric and photoluminescent sensors and components thereof are described in U.S. Pat. Nos. 7,809,441 and 8,126,554, the content of which is herein incorporated by reference.

Optical Excitation and Detection Assemblies

In some embodiments, the optical excitation assembly can include solid state light sources such as GaAs, GaAlAs, GaAlAsP, GaAlP, GaAsP, GaP, GaN, InGaAlP, InGaN, ZnSe, or SiC light emitting diodes or laser diodes that excite the sensing element(s) at or near the wavelength of maximum absorption for a time sufficient to emit a return signal. However, it will be understood that in some embodiments the wavelength of maximum absorption/reflection varies as a function of concentration in the colorimetric sensor.

In some embodiments, the optical excitation assemblies can include other light emitting components including incandescent components. In some embodiments, the optical excitation assemblies can include a waveguide. The optical excitation assemblies can also include one or more bandpass filters, high pass filter, low pass filter, antireflection elements, and/or focusing optics.

In some embodiments, the optical excitation assemblies can include a plurality of LEDs with bandpass filters, each of the LED-filter combinations emitting at a different center frequency. According to various embodiments, the LEDs can operate at different center-frequencies, sequentially turning on and off during a measurement, illuminating the sensing element(s). As multiple different center-frequency measurements are made sequentially, a single unfiltered detector can be used in some embodiments. However, in some embodiments, a polychromatic source can be used with multiple detectors that are each bandpass filtered to a particular center frequency.

The sensing element(s) can include one or more types of indicator beads having embedded therein various types of ion-selective sensors. Physiological analytes of interest can diffuse into and out of the sensing element(s) and bind with an ion-selective sensor to result in a fluorimetric or colorimetric response. Reference analytes can similarly diffuse into and out of the sensing element(s) and serve as a control sample. Exemplary ion-selective sensors are described more fully below.

The optical detection assembly can be configured to receive light from the sensing element(s). In an embodiment, the optical detection assembly can include a component to receive light. By way of example, in some embodiments, the optical detection assembly can include a charge-coupled device (CCD). In other embodiments, the optical detection assembly can include a photodiode, a junction field effect transistor (JFET) type optical sensor, or a complementary metal-oxide semiconductor (CMOS) type optical sensor. In some embodiments, the optical detection assembly can include an array of optical sensing components. In some embodiments, the optical detection assembly can include a waveguide. In some embodiments, the optical detection assembly can also include one or more bandpass filters and/or focusing optics. In some embodiments, the optical detection assembly can include one or more photodiode detectors, each with an optical bandpass filter tuned to a specific wavelength range. For example, in some embodiments, the optical detection assembly can include a colorimetric response detector and a photoluminescent response detector. Each of the colorimetric response detector and the photoluminescent response detector can be a component for receiving light described above, but in some cases can be sensitive to a specific wavelength range, such as a photodiode detector, each with an optical filter to allow it to be tuned to a specific wavelength range. In some embodiments, the colorimetric response detector and the photoluminescent response detector can be integrated as a single unit. In other embodiments, the colorimetric response detector and the photoluminescent response detector can be separate units.

The optical excitation and detection assemblies embodied herein, can be integrated using bifurcated fiber-optics that direct excitation light from a light source to one or more sensing element(s), or simultaneously to sensing element(s) and a reference channel. Return fibers can direct emission signals from the sensing element(s) and the reference channels to one or more optical detection assemblies for analysis by a processor, such as a microprocessor. In some embodiments, the optical excitation and optical detection assemblies are integrated using a beam-splitter assembly and focusing optical lenses that direct excitation light from a light source to the sensing element and direct emitted or reflected light from the sensing element to an optical detector for analysis by a processor.

Ion-Permeable Polymeric Matrix Materials

As referenced above, the analyte window and/or outer barrier layer of each sensing element can be formed of an ion-permeable polymeric matrix material in some embodiments. Suitable polymers for use as the ion-permeable polymeric matrix material can include, but are not limited to polymers forming a hydrogel. Hydrogels herein can include homopolymeric hydrogels, copolymeric hydrogels, and multipolymer interpenetrating polymeric hydrogels. Hydrogels herein can specifically include nonionic hydrogels. In some embodiments, hydrogels herein can be prepared from polymerization of various monomers or macromers including one or more of 2-hydroxyethyl methacrylate (HEMA), 2-hydroxypropyl methacrylate (HPMA), acrylamide, acrylic acid, N-isopropylacrylamide (NIPAm), methoxyl polyethylene glycol monoacrylate (PEGMA), and the like. In some embodiments, polymers can include, but are not limited to polyhydroxyethyl methacrylate (polyHEMA), cellulose, polyvinyl alcohol, dextran, polyacrylamides, polyhydroxyalkyl acrylates, polyvinyl pyrrolidones, and mixtures and copolymers thereof. In some embodiments, suitable polymers for use with the ion-permeable polymeric matrix described herein include those that are transparent.

Physiological Analytes

Examples of physiological analytes that can be measured in accordance with chemical sensors of embodiments herein can include, but are not limited to, electrolytes, hormones, proteins, sugars, metabolites, and the like.

Chemical sensors herein can be directed at a specific analyte or a plurality of different analytes. In an embodiment, the analyte sensed is one or more analytes relevant to cardiac health. In an embodiment, the analyte sensed is one or more analytes indicative of renal health. The analyte sensed can be an ion or a non-ion. The analyte sensed can be a cation or an anion. Specific examples of analytes that can be sensed include acetic acid (acetate), aconitic acid (aconitate), ammonium, blood urea nitrogen (BUN), B-type natriuretic peptide (BNP), bromate, calcium, carbon dioxide, cardiac specific troponin, chloride, choline, citric acid (citrate), cortisol, copper, creatinine, creatinine kinase, fluoride, formic acid (formate), glucose, hydronium ion, isocitrate, lactic acid (lactate), lithium, magnesium, maleic acid (maleate), malonic acid (malonate), myoglobin, nitrate, nitric-oxide, oxalic acid (oxalate), oxygen, phosphate, phthalate, potassium, pyruvic acid (pyruvate), selenite, sodium, sulfate, urea, uric acid, and zinc. Inorganic cations sensed by this method include but not limited to hydronium ion, lithium ion, sodium ion, potassium ion, magnesium ion, calcium ion, silver ion, zinc ion, mercury ion, lead ion and ammonium ion. Inorganic anions sensed by this method include but not limited to carbonate anion, nitrate anion, sulfite anion, chloride anion and iodide anion. Organic cations sensed by this method include but are not limited to norephedrine, ephedrine, amphetamine, procaine, prilocaine, lidocaine, bupivacaine, lignocaine, creatinine and protamine. Organic anions sensed by this method include but not limited to salicylate, phthalate, maleate, and heparin. Neutral analytes sensed by this method include but not limited to ammonia, ethanol, and organic amines. In an embodiment, ions that can be sensed include potassium, sodium, chloride, calcium, and hydronium (pH). In a particular embodiment, concentrations of both sodium and potassium are measured. In another embodiment, concentrations of both magnesium and potassium are measured.

In some embodiments, the analytes can specifically include one or more of sodium ion, magnesium ion, chloride ion, calcium ion, carbonate ion, phosphate ion, sulfate ion, insulin, aldosterone, troponin, glucose, creatinine, and BNP.

In some embodiments, the analytes can specifically include one or more of partial pressure of oxygen ($PaO_2$), partial pressure of carbon dioxide ($PaCO_2$) and oxygen saturation ($O_2Sat$).

The embodiments described herein are not intended to be exhaustive or to limit the invention to the precise forms disclosed in the following detailed description. Rather, the embodiments are chosen and described so that others skilled in the art can appreciate and understand the principles and practices. As such, while aspects have been described with reference to various specific and preferred embodiments and techniques, it should be understood that many variations and modifications may be made while remaining within the spirit and scope herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention claimed is:

1. An implantable medical device comprising:
a first chemical sensor comprising
an optical excitation assembly comprising
a first visible spectrum emitter;
a second visible spectrum emitter; and
at least one of a near-infrared (NIR) emitter and an ultraviolet emitter;
an optical detection assembly comprising
a colorimetric response detector; and
a photoluminescent response detector; and
a multimode sensing element comprising:
a colorimetric response element specific for a first chemical analyte; and
a photoluminescent response element specific for a second chemical analyte
wherein each emitter of the optical excitation assembly is oriented in the implantable medical device to illuminate the multimode sensing element and each detector of the optical detection assembly is oriented in the implantable medical device to receive a response signal from the corresponding response element of the multimode sensing element.

2. The implantable medical device of claim 1, further comprising a low-pass optical filter disposed over or in the photoluminescent response detector.

3. The implantable medical device of claim 1, wherein the colorimetric response detector and the photoluminescent response detector are integrated as a single unit.

4. The implantable medical device of claim 1, wherein the colorimetric response detector and the photoluminescent response detector are separate units.

5. The implantable medical device of claim 1, the multimode sensing element comprising
an outer barrier layer forming a top, a bottom, and opposed sides of the sensing element;
the outer barrier layer defining an interior volume;
wherein the colorimetric response element and the photoluminescent response element are both disposed throughout the interior volume.

6. The implantable medical device of claim 5, wherein the top of the outer barrier layer comprises an analyte window.

7. The implantable medical device of claim 6, wherein the analyte window is opaque to the passage of light.

8. The implantable medical device of claim 1, the multimode sensing element comprising
an outer barrier layer forming a top, a bottom, and opposed sides of the sensing element;
the outer barrier layer defining an interior volume; and
polymeric beads disposed within the interior volume;
wherein the colorimetric response element and the photoluminescent response element are both disposed on or within the polymeric beads.

9. The implantable medical device of claim 8, further comprising
a second chemical sensor comprising
an optical excitation assembly comprising
a first visible spectrum emitter;
a second visible spectrum emitter; and
at least one of a near-infrared (NIR) emitter and an ultraviolet emitter;
an optical detection assembly comprising
a colorimetric response detector; and
a photoluminescent response detector; and
a multimode sensing element comprising:
a colorimetric response element specific for a third chemical analyte; and
a photoluminescent response element specific for a fourth chemical analyte
wherein each emitter of the optical excitation assembly of the second chemical sensor is oriented in the implantable medical device to illuminate the multimode sensing element of the second chemical sensor and each detector of the optical detection assembly of the second chemical sensor is oriented in the implantable medical device to receive a response signal from the corresponding response element of the multimode sensing element of the second chemical sensor.

10. The implantable medical device of claim 8, further comprising a housing and a circuit board disposed within the housing, the housing having a top surface and a bottom surface, the multimode sensing element disposed on or within the top surface.

11. The implantable medical device of claim 10, further comprising an electrode disposed on or within the bottom surface of the housing.

12. The implantable medical device of claim 11, the circuit board comprising a U-shaped portion and an overlapping portion adjacent to the U-shaped portion that overlaps other portions of the circuit board, the electrode attached to the overlapping portion.

13. The implantable medical device of claim 10, wherein the housing comprises a translucent epoxy.

14. The implantable medical device of claim 10, the circuit board comprising side wings angled upward, wherein at least one of the first visible spectrum emitter, the second visible spectrum emitter, the near-infrared (NIR) emitter and the ultraviolet emitter are disposed on a top surface of at least one side wing and pointed inward.

15. The implantable medical device of claim 14, wherein at least one of the first visible spectrum emitter, the second visible spectrum emitter, the near-infrared (NIR) emitter and the ultraviolet emitter are disposed on a top surface of at least one side wing and pointed inward at an angle of 5 to 60 degrees with respect to a plane perpendicular to a middle portion of the circuit board.

16. The implantable medical device of claim 1, further comprising
a translucent optical body member,
wherein the multimode sensing element is disposed on or within a top side of the translucent optical body member and
wherein the optical excitation assembly and the optical detection assembly are disposed on or within a bottom side of the translucent optical body member.

17. The implantable medical device of claim 16, wherein the bottom side of the translucent optical body member comprises one or more flat portions and one or more angled portions, wherein the optical excitation assembly is disposed at least partially on the one or more angled portions and the optical detection assembly is disposed at least partially on the one or more flat portions.

18. The implantable medical device of claim 16, wherein the translucent optical body member comprises a cured translucent adhesive material.

19. The implantable medical device of claim 16, wherein the translucent optical body member comprises a translucent polymer material.

20. The implantable medical device of claim 16, further comprising a plurality of optical shrouds disposed between adjacent elements of the optical excitation assembly and/or optical detection assembly.

* * * * *